United States Patent
Wong et al.

(10) Patent No.: US 12,215,360 B2
(45) Date of Patent: *Feb. 4, 2025

(54) ENCAPSULATION OF DUAL-ENZYME COMPOSITION FOR PREVENTING, TREATING AND/OR ALLEVIATING VEISALGIA AND SYMPTOMS ASSOCIATED THEREWITH

(71) Applicant: Bing Biotech Limited, Hong Kong (HK)

(72) Inventors: Bing Lou Wong, San Diego, CA (US); Sek Lun Law, Hong Kong (HK); Joo Ann Ewe, Hong Kong (HK); Chun Hay Ko, Hong Kong (HK)

(73) Assignee: Bing Biotech Limited, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/465,961

(22) Filed: Sep. 12, 2023

(65) Prior Publication Data

US 2024/0216479 A1  Jul. 4, 2024

Related U.S. Application Data

(63) Continuation-in-part of application No. 17/947,195, filed on Sep. 19, 2022, now Pat. No. 11,795,441.

(Continued)

(51) Int. Cl.
*C12N 9/04* (2006.01)
*C12N 9/02* (2006.01)
*A61K 38/44* (2006.01)

(52) U.S. Cl.
CPC ........ *C12N 9/0006* (2013.01); *C12N 9/0008* (2013.01); *C12Y 101/01001* (2013.01); *A61K 38/44* (2013.01)

(58) Field of Classification Search
CPC .......................... C12N 9/0006; C12N 9/0008
See application file for complete search history.

(56) References Cited

U.S. PATENT DOCUMENTS

2014/0186436 A1* 7/2014 Yang ...................... A61K 47/64
424/94.2
2019/0192444 A1* 6/2019 Barzilay ............... A61K 31/522

FOREIGN PATENT DOCUMENTS

CN  105535945 A  *  5/2016
CN  106387917 A  *  2/2017

OTHER PUBLICATIONS

Liu. English Translation of CN 105535945. retrieved on Jul. 5, 2024.*

(Continued)

*Primary Examiner* — Yong D Pak
(74) *Attorney, Agent, or Firm* — Idea Intellectual Limited; Margaret A. Burke; Sam T. Yip

(57) ABSTRACT

An encapsulated composition for converting ethanol to acetaldehyde and subsequently converting the acetaldehyde to acetate. The composition includes alcohol dehydrogenase and aldehyde dehydrogenase in a molar ratio of approximately 1:3 to approximately 1:51. The composition is encapsulated by a polysaccharide-whey-casein encapsulant such that the encapsulated composition has a controlled release property in the small intestine. The composition reduces symptoms caused by over-consumption of alcohol.

12 Claims, 27 Drawing Sheets

Specification includes a Sequence Listing.

Related U.S. Application Data which is a continuation-in-part of application No. 17/557,046, filed on Dec. 21, 2021, now Pat. No. 11,471,514, which is a continuation-in-part of application No. 17/308,995, filed on May 5, 2021, now Pat. No. 11,208,631.

(56) References Cited

OTHER PUBLICATIONS

Zhao. English translation of CN 106387917. retrieved on Jul. 5, 2024.*

* cited by examiner

ADH:ALDH Ratio in Different Batches of Crude Extracts

| Batch | ADH Activity (U) | ALDH Activity (U) | Ratio | Average Ratio |
|---|---|---|---|---|
| BBT-157 | 2.41±0.24 | 69±0.00 | ~1:29 | |
| NAM1 24/10/22 | 1.81±0.49 | 111±2.83 | ~1:61 | |
| BBT-184 | 3.79±0.17 | 59.2±0.24 | ~1:16 | 1:40.6 |
| 2A | 1.82±0.19 | 83.8±1.18 | ~1:46 | |
| BBT-198 | 1.99±0.17 | 101±1.18 | ~1:51 | |

Add 10 mL of freshly thawed -20°C ADP crude extract into the tube

Measure ADH and ALDH activity by Alcolear ADH and ALDH assay (run 3.5 min, 30 s interval)

ENCAPSULATION OF DUAL-ENZYME COMPOSITION FOR PREVENTING, TREATING AND/OR ALLEVIATING VEISALGIA AND SYMPTOMS ASSOCIATED THEREWITH

CROSS-REFERENCE TO RELATED APPLICATIONS

This application is a continuation in part of U.S. patent application Ser. No. 17/947,195, filed Sep. 19, 2022, which is a continuation in part of U.S. patent application Ser. No. 17/557,046 filed Dec. 21, 2021, and issued as U.S. Pat. No. 11,471,514 on Oct. 18, 2022, which is a continuation-in-part of U.S. patent application Ser. No. 17/308,995 filed May 5, 2021 and issued as U.S. Pat. No. 11,208,631 on Dec. 28, 2021, the disclosures of which are incorporated herein by reference in their entirety.

REFERENCE TO SEQUENCE DISCLOSURE

The sequence listing file under the file name "P1583US05_SEQ LISTING.xml" submitted in ST.26 XML file format with a file size of 4 KB created on Oct. 22, 2024 and filed on Nov. 18, 2024 is incorporated herein by reference.

FIELD OF THE INVENTION

The present invention relates to an effective encapsulation system permitting controlled delivery of a dual-enzyme composition for preventing, treating and/or alleviating veisalgia and symptoms associated therewith, and, more particularly, to assisted enzyme-based breakdown of alcohol/ethanol using the controlled delivery encapsulated dual-enzyme composition.

BACKGROUND

The effect of ingested beverage alcohol (ethanol) on different organs in human body, including the brain/Central Nervous System, liver & pancreas, depends on the ethanol concentration intake and the duration of exposure. Both of these variables are affected by the absorption of ethanol into the blood stream and tissues as well as by ethanol metabolism. The primary enzymes in the human body involved in ethanol metabolism are Alcohol Dehydrogenase ("ADH") and Aldehyde Dehydrogenase ("ALDH"). The main pathway of ethanol metabolism involves its oxidation to acetaldehyde, a reaction that is catalysed by ADH and co-enzyme NAD+. In a second reaction catalyzed by ALDH and co-enzyme NAD+, acetaldehyde is oxidized to acetic acid. This metabolism is illustrated as FIG. 1. The mechanism through which ADH and ALDH influences alcoholism risk is thought to involve local elevation of acetaldehyde levels, resulting either from a more rapid ethanol oxidation or from a slower acetaldehyde oxidation. Acetaldehyde is a toxic substance whose accumulation leads to highly adverse reactions that include facial flushing, nausea, rapid heart rate and veisalgia, and symptoms associated therewith (FIG. 1).

Recently, many people use over-the-counter pain relievers, like aspirin or acetaminophen, to relieve veisalgia and symptoms associated therewith. It is important to recognize that the combination of alcohol and acetaminophen can be toxic to the liver. Furthermore, there is no medication for acute alcohol intoxication. Haemodialysis is the only option in emergency cases, especially in the US, where the medicine Metadoxin has not been approved by the FDA. Consequently, the development of innovative preventive measures which can effectively minimize the risk of potential health hazards brought about by drinking alcohol has become a very important strategy to lessen the burden on the overall economy. There is a huge void in the healthcare market for a product which is effective, safe, and convenient for daily use as a prophylaxis measure for casual and frequent alcohol drinkers and patients suffering from alcohol use disorder.

As seen from the various alcohol ingestion-related problems, there is a need in the art to enhance the breakdown of alcohol in the human body. Enhanced breakdown of alcohol and alcohol metabolism products would reduce long-term harmful effects from alcohol such as liver damage, and short-term effects such as veisalgia and alcohol poisoning. Thus, there is a need in the art for compositions that can enhance the breakdown of alcohol in the human body that are low-cost and have minimal side effects.

In addition, certain populations may experience spontaneous production of alcohol in the gut, leading to a common condition known as Non-Alcoholic Fatty Liver Disease ("NAFLD"). A composition that would metabolize such spontaneously accumulated alcohol would relieve the suffering of large numbers of persons with this ailment.

Additionally, there is a need in the art for an effective encapsulation technique for compositions that can treat symptoms of alcohol consumption. Such compositions must be capable of controlled delivery and be able to withstand the acidic environment of the stomach.

SUMMARY OF THE INVENTION

In one aspect, there is provided a composition including two exogenous enzymes from animals for consumption by human beings before and/or after consuming alcohol to prevent, treat and/or alleviate veisalgia and/or symptoms associated therewith arising from or caused by consumption of alcohol or production of alcohol in the body in patients with NAFLD, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and NAD$^+$/NADH, and wherein the first enzyme to the second enzyme is in a molar ratio of 1:3-51 in the composition in order to avoid local elevation of the first metabolite in the human being after consumption of alcohol.

The present invention further provides a unique polysaccharide-whey-casein system that provides protection against ethanol and gastric acid for the enzyme-containing compositions. The encapsulated composition may include 0.6% w/v alginate or less, 5% w/v whey protein or less and 50% w/v milk or less with the enzyme-containing compositions forming the balance.

In one aspect, the present invention provides an encapsulated composition for converting ethanol to acetaldehyde and subsequently converting the acetaldehyde to acetate. The composition includes alcohol dehydrogenase and aldehyde dehydrogenase in a molar ratio of approximately 1:3 to approximately 1:51. The composition is encapsulated by a polysaccharide-whey-casein encapsulant such that the encapsulated composition is a controlled release composition in the small intestine.

In a further aspect, the encapsulated composition may include alcohol dehydrogenase and aldehyde dehydrogenase sourced from the same or two or more different animal origins.

The encapsulated composition may include the alcohol dehydrogenase and aldehyde dehydrogenase sourced from the same animal origin, and the animal is selected from a bovine, ovine, equine, or galline animal.

The encapsulated composition may include alcohol dehydrogenase and aldehyde dehydrogenase sourced from different animal origins, and the animals are selected from two or more of bovine, ovine, equine, galline or any combination thereof.

The encapsulated composition may include alcohol dehydrogenase and aldehyde dehydrogenase are sourced from the livers of animals.

The encapsulated composition may include alcohol dehydrogenase and aldehyde dehydrogenase sourced from Baker's yeast (*S. cerevisiae*).

The encapsulated composition may include 0.6% w/v alginate or less, 5% w/v whey protein or less and 50% w/v milk or less, with a balance being alcohol dehydrogenase and aldehyde dehydrogenase in a molar ratio of approximately 1:3 to approximately 1:51.

The encapsulated composition may have a particle size in a range of 0.2-2 mm.

The encapsulated composition may include a polysaccharide that is one or more of alginate, chitosan, pectin, starch, cellulose, agarose, xanthan gum, carrageenan, or guar gum.

The encapsulated composition may include a polysaccharide that is sodium alginate.

In a further aspect, the present invention may provide a method of preparing the encapsulated composition by forming a mixture of polysaccharide, whey, and milk followed by introducing an alcohol dehydrogenase and aldehyde dehydrogenase composition in a molar ratio of approximately 1:3 to approximately 1:51 to the mixture to form particles of alcohol dehydrogenase and aldehyde dehydrogenase composition in a molar ratio of approximately 1:3 to approximately 1:51 surrounded by an encapsulant formed from the polysaccharide, whey, and milk mixture.

DEFINITIONS

Figure 1:
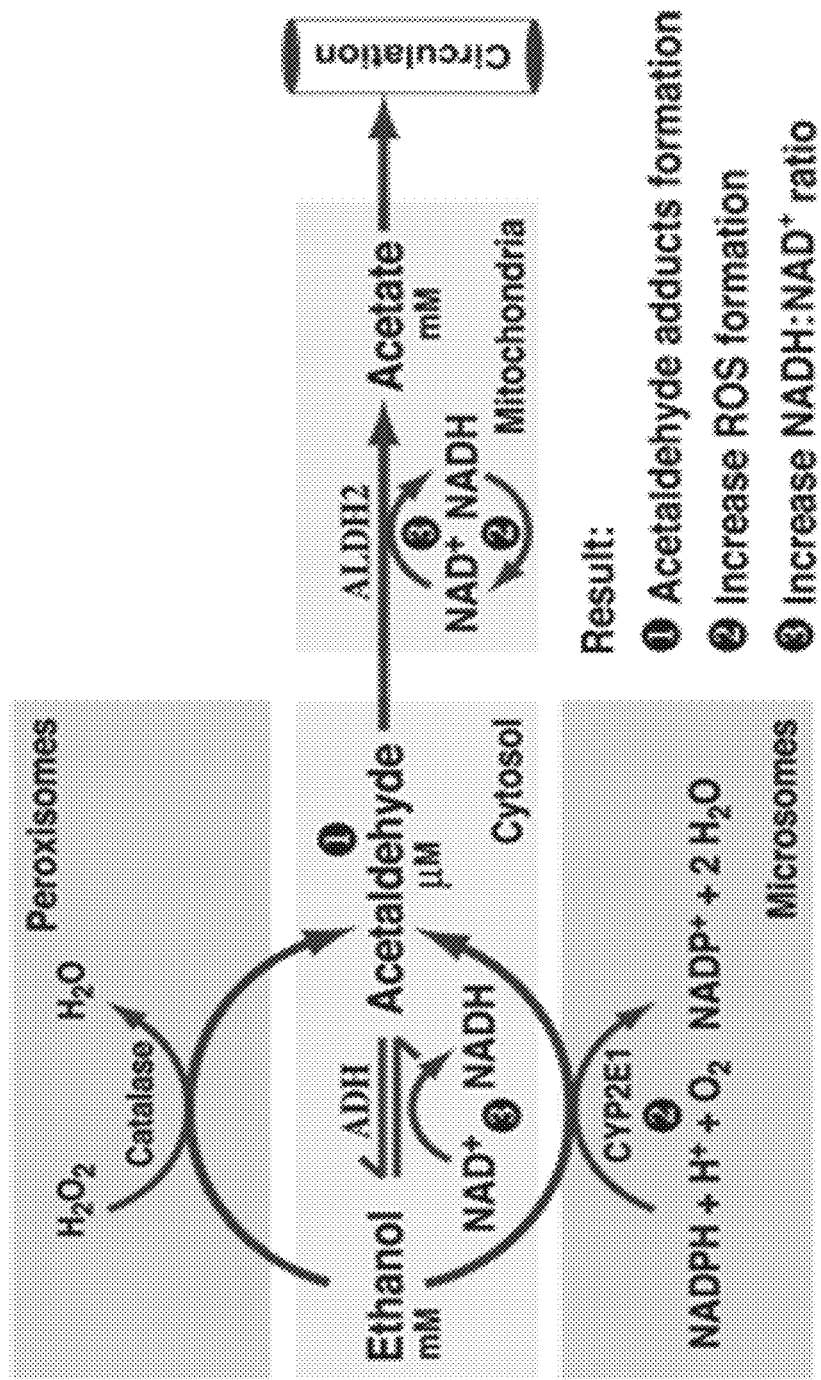
FIG. 1 schematically illustrates the general mechanism of how ADH and ALDH2 metabolize alcohol in a human body.
Figure 2:
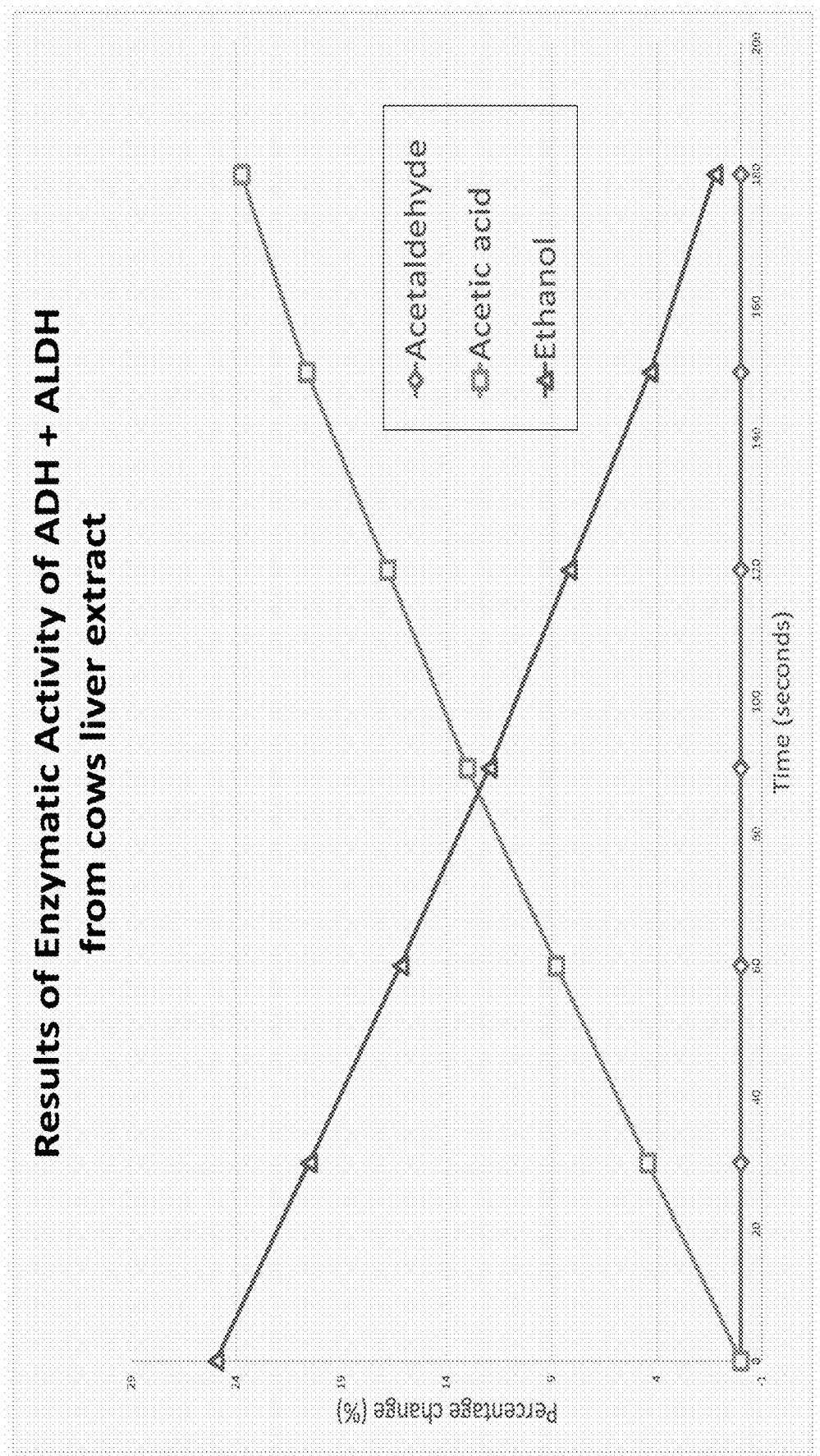
FIG. 2 shows the result of in vitro enzymatic activity of the present composition from extract of cows' liver in terms of the change in concentration of alcohol and its by-products or metabolites over time.
Figure 3:
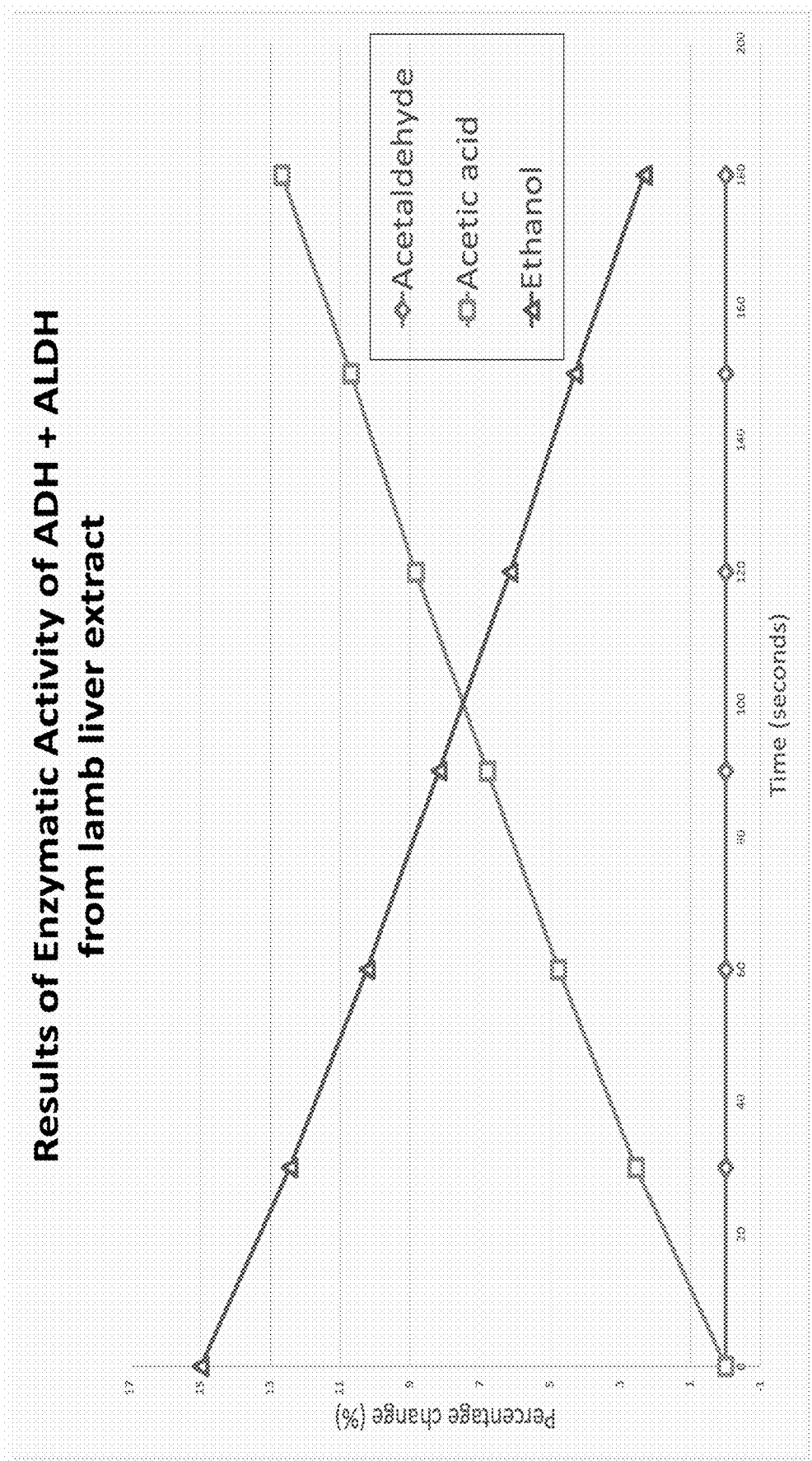
FIG. 3 shows the result of in vitro enzymatic activity of the present composition from extract of lambs' liver in terms of the change in concentration of alcohol and its by-products or metabolites over time.
Figure 4:
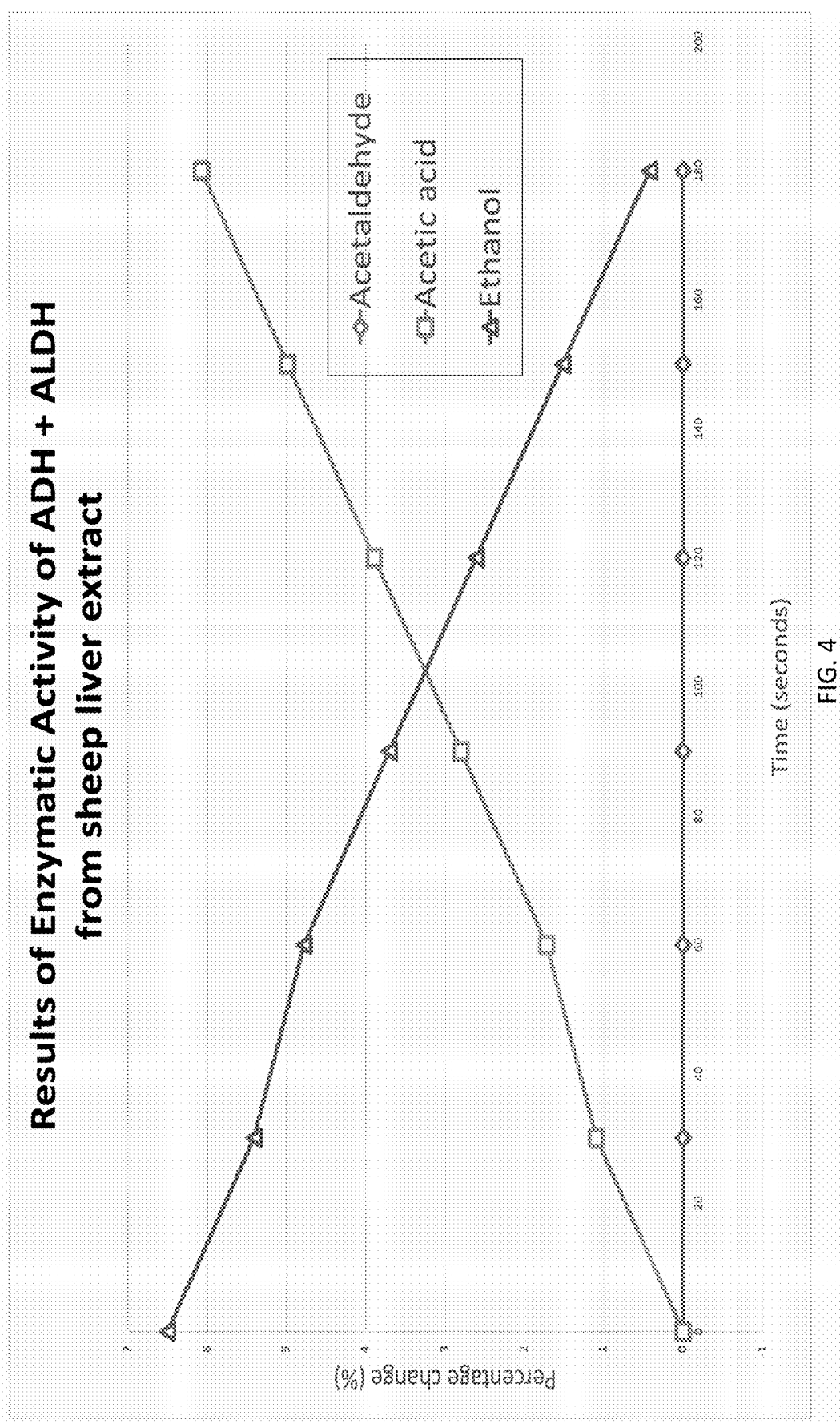
FIG. 4 shows the result of in vitro enzymatic activity of the present composition from extract of sheep' liver in terms of the change in concentration of alcohol and its by-products or metabolites over time.
Figure 5:
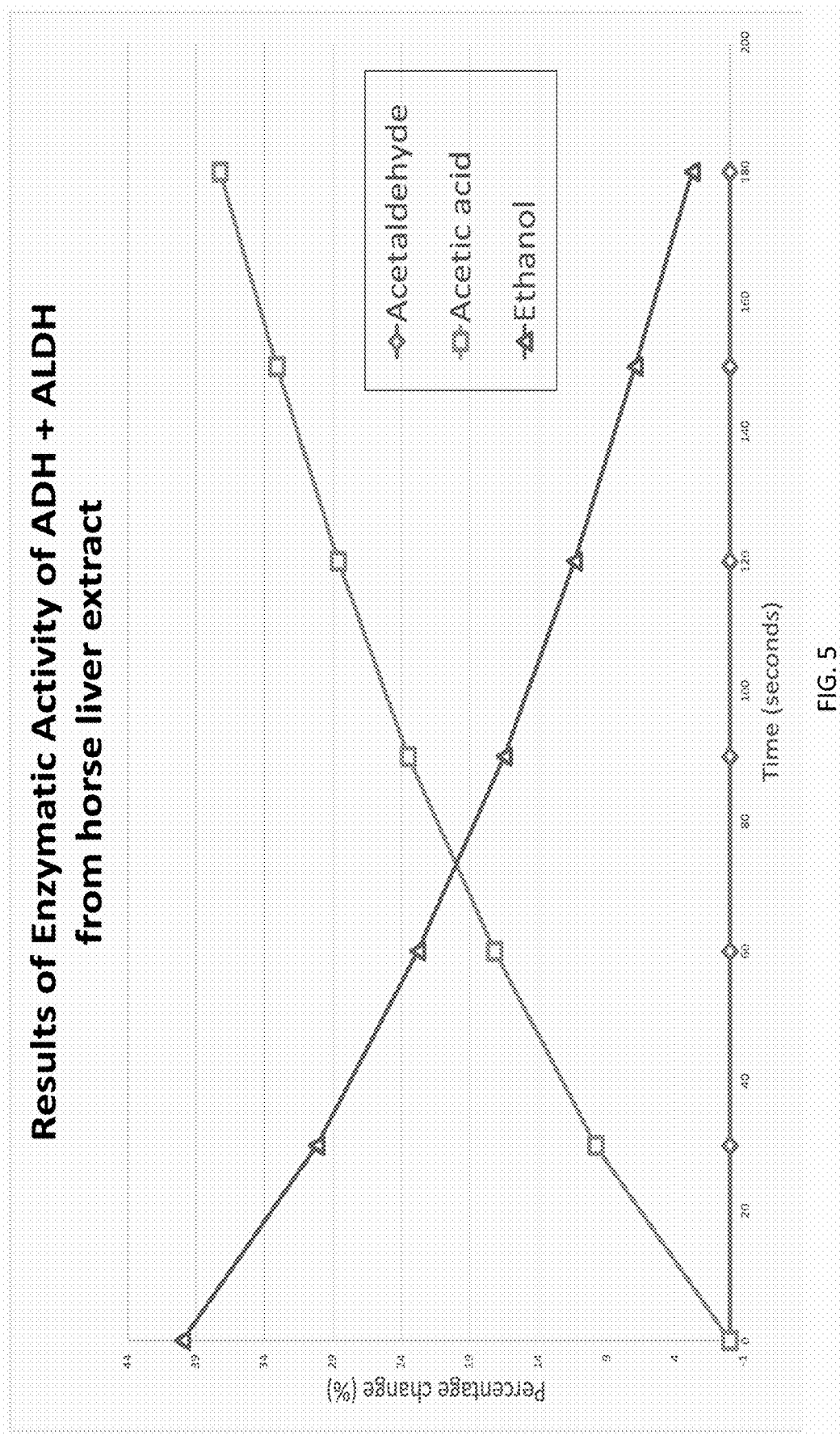
FIG. 5 shows the result of in vitro enzymatic activity of the present composition from extract of horse liver in terms of the change in concentration of alcohol and its by-products or metabolites over time.
Figure 6:
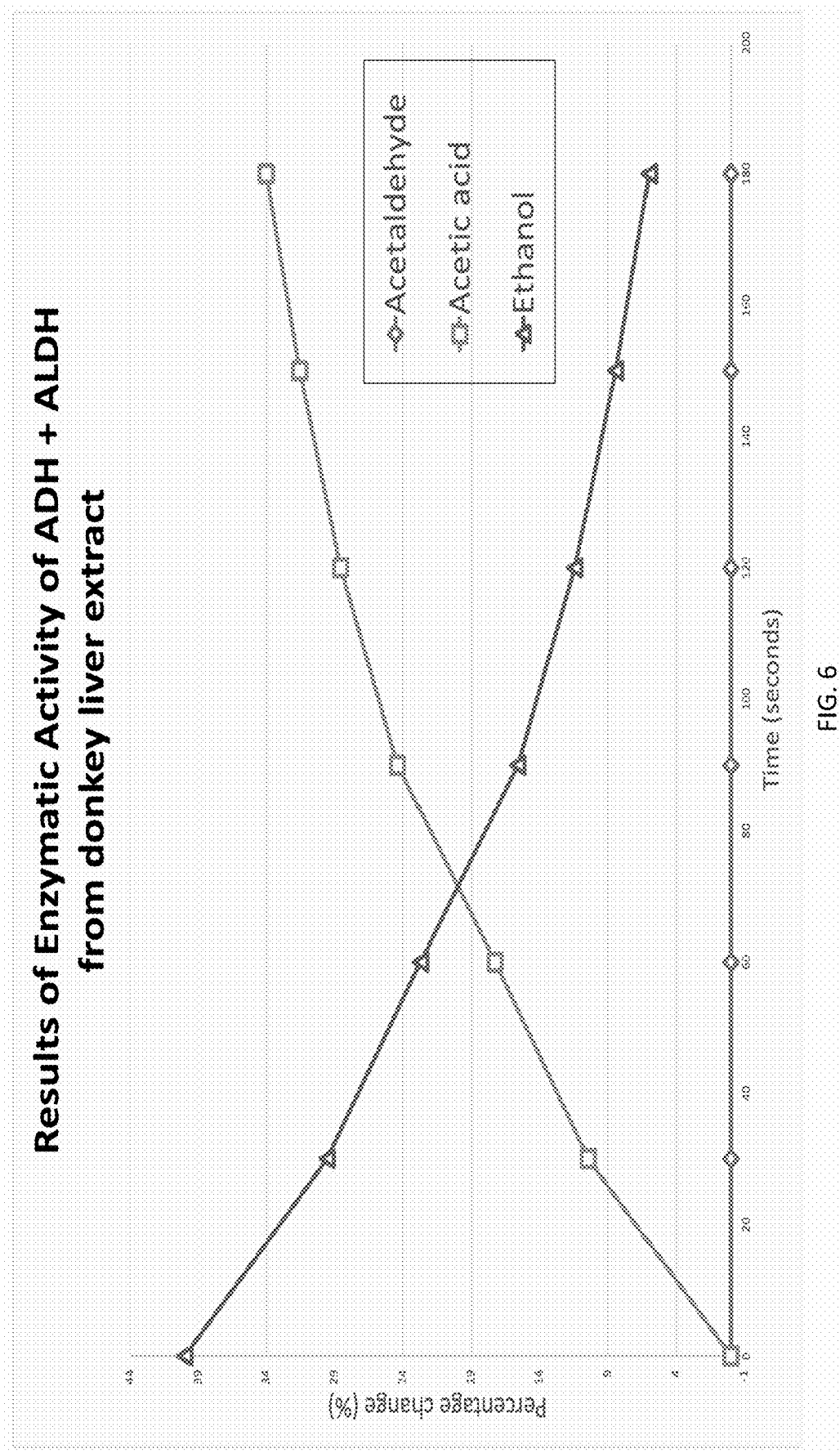
FIG. 6 shows the result of in vitro enzymatic activity of the present composition from extract of donkey liver in terms of the change in concentration of alcohol and its by-products or metabolites over time.
Figure 7:
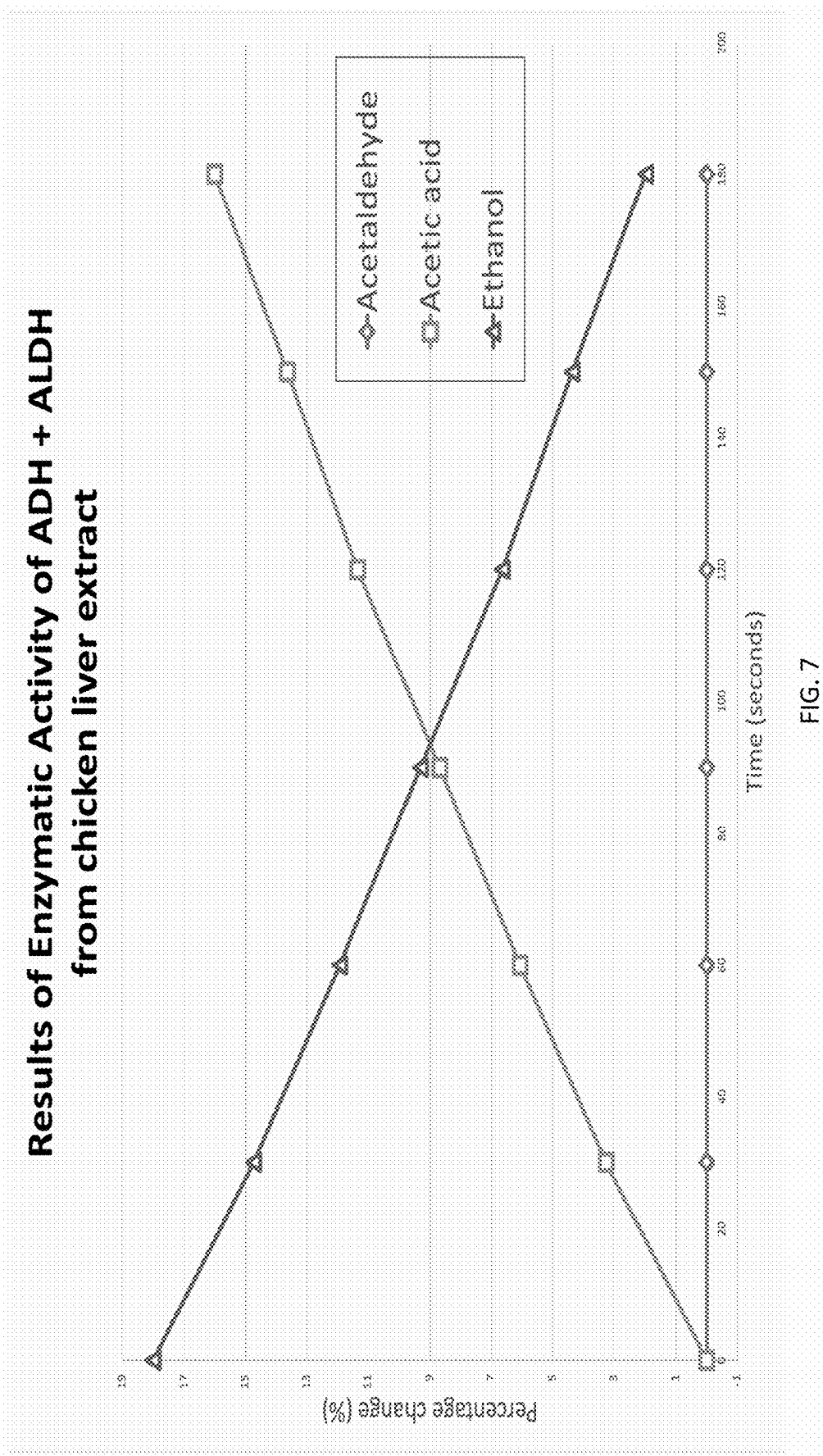
FIG. 7 shows the result of in vitro enzymatic activity of the present composition from extract of chicken liver in terms of the change in concentration of alcohol and its by-products or metabolites over time.

The following abbreviations and their corresponding long expressions are used herein interchangeably:
ADH—Alcohol Dehydrogenase
AHSS—Alcohol Hangover Severity Scale
ALDH—Aldehyde Dehydrogenase
AUD—Alcohol Use Disorder
FDA—Food and Drug Administration
I.M.—intramuscular
I.V.—intravenous
NAFLD—non-alcoholic fatty liver disease
US—United States
WHO—World Health Organization Throughout the present application, any numerical value or range presented with the term "about', "approximately", or alike, is understood by a skilled artisan to refer to also include those values near a recited value or near the upper and lower limits of a recited range. For example, "about 40 [units]" may mean within +25% of 40 (e.g., from 30 to 50), within ±20%, ±15%, ±10%, ±9%, ±8%, ±7%, ±7%, ±5%, ±4%, ±3%, ±2%, ±1%, less than ±1%, or any other value or range of values therein or therebelow. Also, the terms "about" and "approximately" are used herein interchangeably throughout the present application.

Further, the term "approximately" is to cover minor variations to the composition that do not affect the activity of the overall composition. That is, minor changes that produce the same effects as the claimed composition are intended to be included in the scope of the appended claims.

For numerical ranges provided for certain quantities, it should be understood that these ranges also cover subranges therein. For example, the range "from 50 to 80" includes all possible ranges therein (e.g., 51-79, 52-78, 53-77, 54-76, 55-75, 70-70, etc.).

Furthermore, all values within a given range may be an endpoint for the range encompassed thereby (e.g., the range 50-80 includes the ranges with endpoints such as 55-80, 50-75, etc.).

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR, Raman spectroscopy or XRPD; and to indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. As used herein, a tilde (i.e., "~") preceding a numerical value or range of values indicates "about" or "approximately".

Further, it is understood that, when active ingredient ranges are applied to human populations, there is a wide range of body weights that receive approximately the same dosage. Therefore, the amount of active ingredient per kg of body weight has a natural range when a dose of, for example, 100 mg is applied to patients with weights ranging from 50 kg to over 100 kg. Therefore, the experimental results shown in the present disclosure can naturally be extrapolated over the ranges described as "approximate" and "about" as set forth above.

DETAILED DESCRIPTION

The Detailed Description first describes the enzyme-containing compositions in detail in the first section. In the second section, the Detailed Description describes the encapsulation techniques for the enzyme-containing coating compositions. The Examples similarly first present techniques for forming the enzyme-containing compositions followed by techniques for forming the encapsulated compositions and methods for coating the enzyme-containing compositions.

I. Enzyme-Containing Compositions:

1. Mechanisms of the Present Invention:

Enzymes are macromolecular biological catalysts, which can accelerate chemical reactions in the human body. Almost all metabolic processes in cells need enzyme catalysis in order to occur at rates fast enough to sustain life. Enzymes are known to catalyse more than 5,000 biochemical reactions. Most enzymes are proteins, and the specificity comes from their unique three-dimensional structures. As many enzymes are naturally produced by the human body, they are safe to use as supplements that may be ingested.

The present invention focuses on two enzymes for alcohol metabolism, namely Alcohol Dehydrogenase ("ADH") and Aldehyde Dehydrogenase ("ALDH"). ADH is an enzyme found primarily in the liver and stomach that converts ethanol to acetaldehyde, a toxin which is then further broken down by ALDH to acetate, which can be converted to carbon dioxide and water. These two enzymes were studied using in vitro assays, proving that the corresponding enzymatic activity is highly potent, and could potentially be used to enhance the degradation of alcohol in the human body for alcohol drinkers to prevent as well as treat and/or alleviate veisalgia and symptoms associated therewith. These enzymes may also be used to treat those whose faulty microbiomes are overproducing ethanol from non-alcohol-based food and beverages leading to non-alcoholic fatty liver disease ("NAFLD"). Thus, the compositions may be effective in reducing or preventing NAFLD.

In one aspect, ADH and ALDH were tested, in vitro, to determine activity on ethanol substrates. The ADH and ALDH were sourced from mammal or aves livers, a plentiful natural source for the starting material that can contribute to production of a low-cost oral supplement.

The enzymes tested use a molar ratio of ADH and ALDH ranging from approximately 1:3 to approximately 1:51, to enable the second step of the enzymatic alcohol degradation process to be the dominant enzymatic reaction. The rationale for developing such a formulation is to prevent the accumulation of acetaldehyde, which is the major cause of veisalgia and symptoms associated therewith. Using this formulation, acetaldehyde, the breakdown product from alcohol in the first step of enzymatic process, is effectively degraded to acetic acid and eventually water and carbon dioxide.

2. Formulations Used in the Present Invention

The ADH and ALDH from the livers of nine animals including cow, lamb, sheep, pig, horse, donkey, chicken, duck, and goose were tested, in vitro, to determine activity on alcohol and aldehyde substrates in order to find out the molar ratio of ADALAT from their liver extract. Pig, duck, and goose livers were found not to contain ALDH. Other species that have both ADH and ALDH within the range of 1:3 to 1:51 may also be used in the present invention.

Further, based on the ranges of ratios of ADH:ALDH determined from various animal species (1:3 to 1:51), the ratios may also be recreated using other sources of ADH and ALDH. For example, ADH and ALDH may be sourced from Baker's yeast (*S. cerevisiae*). Thus, both animal and non-animal sources of ADH and ALDH may be used to break down alcohol/ethanol in the present invention. That is, each ratio between 1:3 and 1:51, whether from 100 percent of one species, a mixture of two or more species, a mixture of animal and non-animal sources of ADH and ALDH or purely non-animal sources of ADH and ALDH such as Baker's yeast, may be used to convert ethanol to acetaldehyde and subsequently convert the acetaldehyde to acetate.

2. Controlled Delivery of the Composition of the Present Invention

The present invention also relates to encapsulation of the above ADH:ALDH-containing materials in such a manner that the active ingredients are released in a controlled manner in the small intestine. In general, the present invention uses a polysaccharide-in-whey encapsulation technique to provide for the controlled release. In particular, alginate-in-whey encapsulation in used for encapsulation in the examples below. However, it is possible to use other polysaccharides depending upon factors such as the desired release profile, environmental conditions, and the specific properties of the encapsulated materials. These other polysaccharides may include one or more of chitosan, pectin, starch, cellulose, agarose, xanthan gum, carrageenan, guar gum. These other polysaccharides may also be combined with alginate in the present encapsulation system. Thus, although the term "alginate-in-whey" is used in the description below, it is understood that this term also includes these other polysaccharides.

An Alginate-in-Whey protein Emulsion (AWE) system that provides protection against ethanol and gastric acid and targeted release for the compositions of the present invention, designated as "Alcohol Degradation Protein" (ADP), in the description below. The ADP is the dual-enzyme-based protein breaking down excess alcohol. A typical ratio of alcohol dehydrogenase (ADH) and acetaldehyde dehydrogenase (ALDH) ranges from 1:16-1:61, on average in a molar ratio of 1:40.6. Ionic gelled polyanionic charge polymer is included to encapsulate the ADP, protecting it from gastric acid and ethanol degradation. An amphoteric binder is added to connect the polymer and the emulsion. Emulsion provides a small intestine targeted release by breaking down when in contact with bile salt. The system includes a formulation that is both gastric acid and ethanol resistant, and possesses targeted release properties.

Alginate is a naturally occurring polysaccharide derived from brown seaweed strains. It has gained significant attention in the field of pharmaceutical and food industries due to its unique properties, including its ability to form gel-like structures in the presence of divalent cations, such as calcium. Whey protein is a high-quality protein derived from milk that has excellent emulsifying and encapsulation properties.

Alginate in Whey Protein Emulsion (AWE) is a composite system where alginate is used in combination with whey protein to encapsulate and protect pharmaceutical products. This system involves the formation of emulsion droplets containing the ADP composition (ADH/ALDH) within a matrix of whey protein and alginate. The emulsion droplets are stabilized by the emulsifying properties of whey protein, while alginate contributes to the formation of a protective gel layer around the droplets.

Protection from Gastric Acid Degradation:

In the context of pharmaceutical encapsulation, one of the critical challenges is to protect the encapsulated drug from degradation in the harsh acidic environment of the stomach (having a pH on the order of 3 or less). The Alginate in Whey Protein Emulsion (AWE) addresses this challenge through the following mechanisms:

Physical Barrier: The alginate and whey protein matrix forms a protective barrier around the pharmaceutical compound, preventing direct exposure to gastric acid and enzymes. This physical barrier helps shield the encapsulated active ingredients from acid-induced degradation.

Gel Formation: Alginate has the ability to gel in the presence of calcium ions, forming a stable hydrogel. When the AWE reaches the stomach, the release of calcium ions triggers the formation of a protective gel layer around the emulsion droplets. This gel layer acts as an additional barrier against acid penetration and enzymatic degradation.

Delayed Release: The gel layer formed by alginate also contributes to delaying the release of the encapsulated material. As the gel gradually dissolves in the stomach, the drug release is controlled, preventing a rapid and complete release that could lead to degradation.

Release in the Small Intestine:

After passing through the stomach, the AWE system reaches the small intestine, where most nutrient absorption occurs. The controlled release of the encapsulated active ingredients in the small intestine is facilitated by the following mechanisms:

pH Sensitivity: The pH of the small intestine is higher (less acidic, typically with a pH of greater than 6) compared to the stomach. Alginate gels are sensitive to pH changes and can dissolve or weaken in less acidic environments. As the AWE system enters the small intestine, the gradual increase in pH triggers the weakening and dissolution of the alginate gel, allowing the release of the encapsulated active ingredients.

Digestive Enzymes: The small intestine is rich in digestive enzymes that can further degrade the alginate and whey protein matrix. The breakdown of this matrix contributes to the controlled release of the active ingredient from the emulsion droplets. In the present invention, bile salts in the small intestine will break down the encapsulant, gradually releasing the material containing the ADP (ADH/ALDH active ingredients).

Diffusion and Permeability: The partially dissolved or weakened alginate gel, along with the action of digestive enzymes, increases the permeability of the AWE system. This allows the released ADP to diffuse out of the emulsion droplets and become available for absorption through the intestinal wall.

Tailored Release Profiles: The AWE system of the present invention can influence the overall release profile of the encapsulated material. Depending on the selected amounts of alginate and whey protein, the rate of gel dissolution can be modified, further delaying drug release in the stomach, and facilitating a more controlled release in the small intestine.

Synergistic Encapsulation Effects: Combining the different emulsifiers in the encapsulation system of the present invention leads to synergistic effects, such as improved encapsulation efficiency and prolonged drug retention within the emulsion droplets. The interaction between the various polymers can create a more complex and versatile matrix that adapts to different physiological conditions.

Tuning Drug Release Kinetics: The ionic gelled polyanionic charge polymer/binder system allows for fine-tuning the release kinetics of the encapsulated material. Depending on the polymer's properties and the desired therapeutic outcome, the drug release rate can be adjusted to achieve specific pharmacokinetic profiles.

Targeted Delivery: The combined use of multiple polymers can potentially offer opportunities for targeted drug delivery to specific regions of the gastrointestinal tract. By designing the polymer interactions and release mechanisms appropriately, it may be possible to achieve site-specific drug release, optimizing therapeutic efficacy.

Casein proteins are also added to the emulsion of alginate, whey protein, and ADP containing material in an amount of up to 50 volume The casein proteins may be added at the same time or, alternatively, may follow an initial encapsulation by an AWE emulsion. In particular, a multilayer coating structure may optionally be formed with an alginate-in-whey structure being a layer immediately next to the ADP for initial encapsulation, with a casein-including layer as a second layer to provide additional benefits as described below.

Protein-Dominated Matrix: Casein and whey proteins can form a protein-dominated matrix along with alginate. This matrix can have varying levels of protein aggregation and interactions, which can influence the release kinetics of the encapsulated drug.

Physiological pH Changes: Casein and whey proteins are sensitive to pH changes. In the stomach, where the pH is low, casein proteins may aggregate and further enhancing gastric acid protection. As the pH increases in the small intestine, the protein matrix can undergo structural changes, potentially leading to ADP release due to protein unfolding or disassembly.

Selective Enzymatic Degradation: Casein and whey proteins are subject to enzymatic degradation by proteases in the gastrointestinal tract. Depending on the specific protein used, the matrix could be designed to undergo controlled enzymatic degradation in the small intestine, contributing to the release of the encapsulated ADP.

Surface Modification and Targeting Ligands: Depending on the formulation, casein may also allow for surface modification with targeting ligands that can enhance tissue-specific adhesion or cellular uptake. This could potentially contribute to targeted drug delivery to specific sites in the gastrointestinal tract.

Improved Stability: Casein-based layers can provide enhanced protection and stability to the encapsulated ADP, preventing degradation due to environmental factors like moisture or oxygen.

While not being bound by any particular theory, the inventive encapsulation system may provide a layer-by-layer encapsulation. The polyanionic charge of alginate binds to amphoteric polyelectrolytes, alcohol degradation protein (ADP), protecting it from gastric acid and ethanol. The addition of whey protein, with its amphoteric properties, favors binding of protein on the alginate surface. When a milk/casein emulsion is added, the lipids and protein in milk further protect the ADP from digestion. Moreover, calcium ions in the milk emulsion diffuse through the whey protein to crosslink with the alginate in the innermost layer, forming an alginate box surrounding the ADP, reinforcing the acid and ethanol-resistant protection. The resulting product demonstrates a controlled release. That is, upon reaching the small intestine, the fat emulsified by the enzymes slowly causes disintegration of the encapsulated structure, protein, and then the alginate box to release the active ingredients.

The use of whey protein/alginate and casein/alginate in the encapsulation system takes advantage of whey's solubility and rapid gelation properties, providing immediate protection to an encapsulated ingredient while a casein-based gel can offer slower release and enhanced stability. Thus, the polysaccharide-whey-casein encapsulant of the present invention provide a unique controlled-release of the ADP composition in the small intestine.

The following examples first describe the ADP compositions and their ADH/ALDH ratios, and next describe encapsulation techniques for the ADP compositions.

Examples I: Compositions Containing the Desired ADH:ALDH Ratios

Example 1—Cows (Bovine)

The cow liver is sourced from Australia in frozen form. The in vitro enzymatic activity results from liver of cows (from dry powder of cows' liver extract when the concentration is about 50 mg/ml) for ADH is on average 3.25 Unit and for ALDH is on average 91.31 Unit. The molar ratio of ADH:ALDH is rounded up to 1:28.

Example 2—Lamb (Ovine)

The lamb liver is sourced from Australia in frozen form. The in vitro enzymatic activity results from liver of lamb (from dry powder of lamb liver extract when concentration is about 50 mg/ml) for ADH is on average 1.60 Unit and for ALDH is on average 63.09 Unit. The molar ratio of ADH:ALDH is rounded up to 1:39.

Example 3—Sheep (Ovine)

The sheep liver is sourced from Australia in frozen form. The in vitro enzymatic activity results from the livers of sheep (from dry powder of sheep liver extract when concentration is about 50 mg/ml) for ADH is on average 0.80 Unit and for ALDH is on average 40.65 Unit. The molar ratio of ADH:ALDH is rounded up to 1:51.

Example 4—Pig (Swine)

The pig liver is sourced from local markets in Hong Kong and is fresh. Pig liver was determined to only have the ADH enzyme without the ALDH enzyme. The in vitro enzymatic activity results from the liver of pigs (from dry powder of pig liver extract when concentration is about 50 mg/ml) for ADH is 3.51 Unit. As seen in FIG. 9, there is no increase in acetate due to the liver not containing ALDH.

Example 5—Horse (Equine)

The horse liver is sourced from China in frozen form. The in vitro enzymatic activity results from the livers of horses (from supernatant of crude extract of horse liver) for ADH is 9.04 Unit and for ALDH is 42.67 Unit. The molar ratio of ADH:ALDH is rounded up to 1:5.

Example 6—Donkey (Equine)

The donkey liver is sourced from China in fresh form. The in vitro enzymatic activity results from livers of donkeys (from supernatant of crude extract of donkey liver) for ADH is 9.87 Unit and for ALDH is 184.00 Unit. The molar ratio of ADH:ALDH is rounded up to 1:19.

Example 7—Chicken (Galline)

The chicken liver is sourced from local markets in Hong Kong in fresh form. The in vitro enzymatic activity results from livers of chickens (from supernatant of crude extract of chicken liver) for ADH is 2.96 Unit and for ALDH is 8.09 Unit. The molar ratio of ADH:ALDH is rounded up to 1:3.

Example 8—Duck (Anas)

Figure 8:
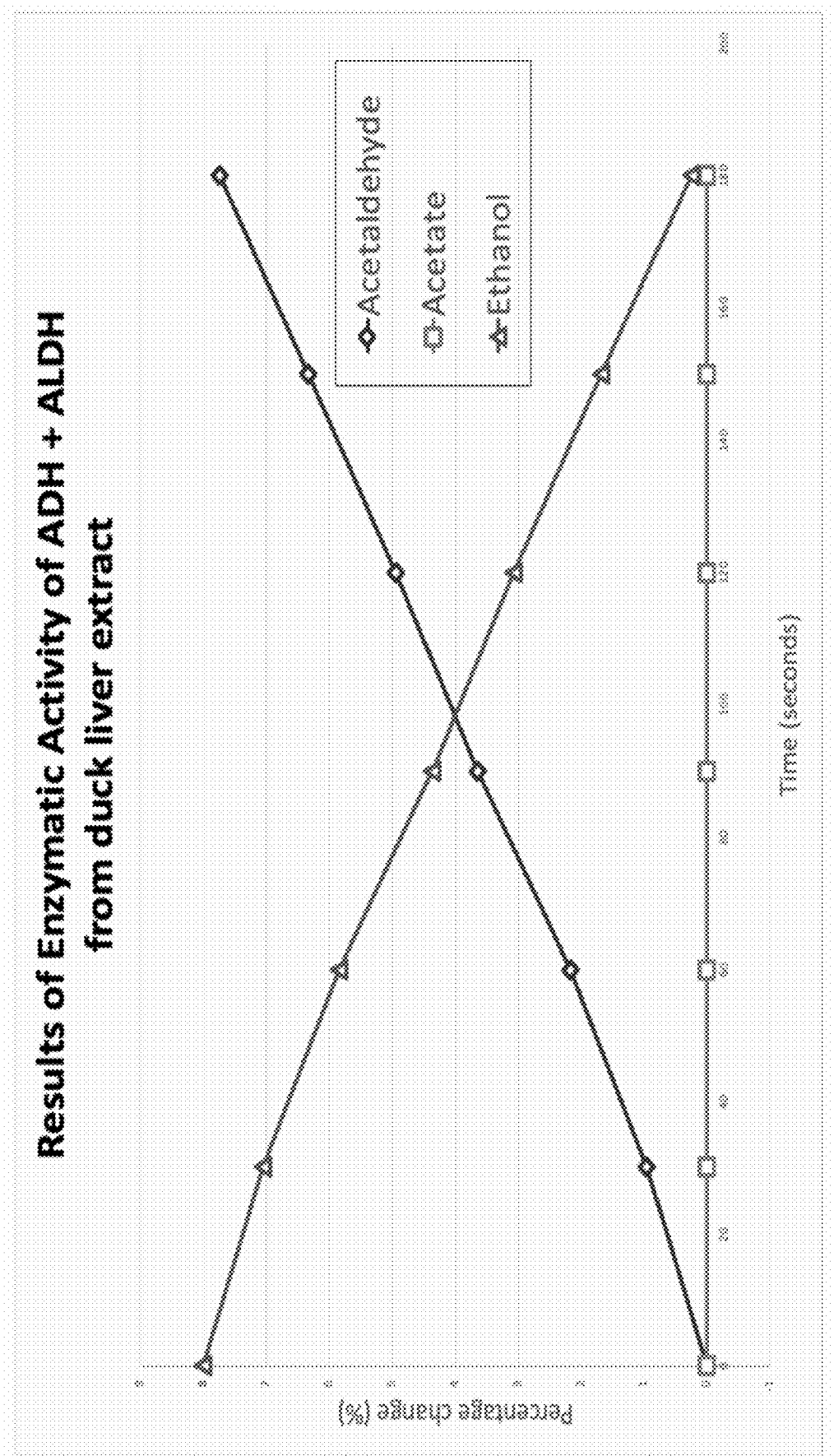
FIG. 8 shows the result of in vitro enzymatic activity from an extract of duck liver in terms of the change in concentration of alcohol and its by-products or metabolites over time showing no increase in acetate due to the liver not containing ALDH.
Figure 9:
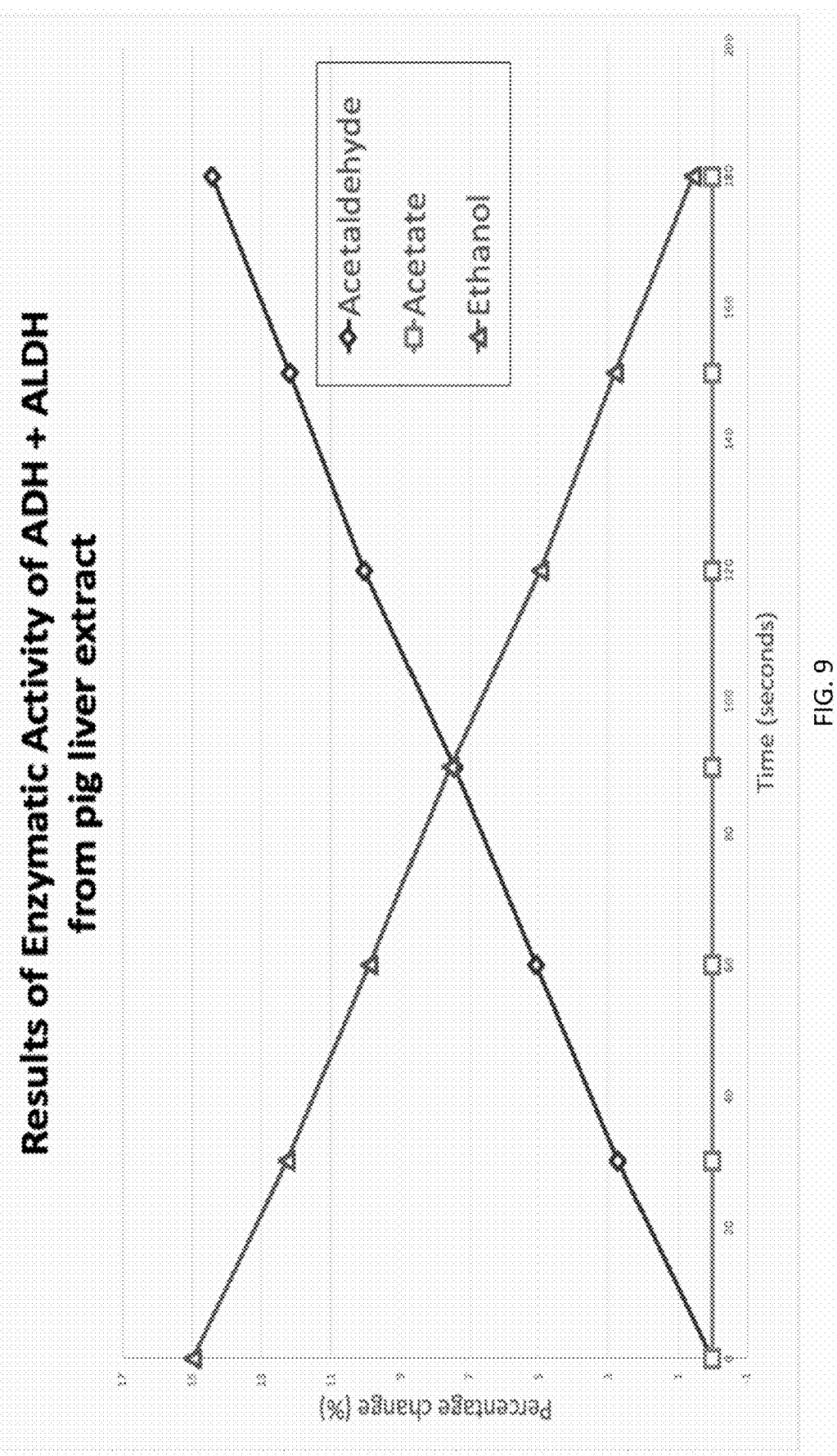
FIG. 9 shows the result of in vitro enzymatic activity from an extract of pig liver in terms of the change in concentration of alcohol and its by-products or metabolites over time showing no increase in acetate due to the liver not containing ALDH.

The duck liver is sourced from local markets in Hong Kong in fresh form. Duck liver was determined to have only ADH enzyme without ALDH enzyme. The in vitro enzymatic activity results from livers of ducks (from supernatant of crude extract of duck liver) for ADH is 1.32 Unit. As seen in FIG. 8, there is no increase in acetate due to the liver not containing ALDH.

Example 9—Goose (Anser)

The goose liver is sourced from Hungary in frozen form. The goose liver is foie gras and contains too much fat in the liver, as a result, in vitro test of ADH & ALDH enzymes cannot be done.

Table 1 summarizes the in vitro test results of the molar ratio of ADH:ALDH in each animal.

TABLE 1

| Animal | Ratio ADH:ALDH |
|---|---|
| Cows | 1:28 |
| Lamb | 1:39 |
| Sheep | 1:51 |
| Pig | 1:0 |
| Horse | 1:5 |
| Donkey | 1:19 |
| Chicken | 1:3 |
| Duck | 1:0 |
| Goose | 0:0 |

The enzymes extracted from the livers of the nine animals were tested in vitro and only six of them including cows, lamb, sheep, horse, donkey, and chicken were found to contain both ADH and ALDH. From the test results, the range of the molar ratio of ADH:ALDH among these six animals is from approximately 1:3 to approximately 1:51.

The in vitro enzymatic activity of liver extract from cows, lamb, sheep, horse, donkey, and chicken are illustrated in Table 1, FIG. 2 to FIG. 7 respectively.

From the results, it can be concluded that the livers of herbivores contained both ADH and ALDH; for omnivores that eat both plant and animal matter, their livers contained only ADH but did not have ALDH.

Example 10

It is determined that by mixing the various species' extracts, a complete range of ADH:ALDH ratios from 1:3 to 1:51 may be formed. As seen below, a general formula is presented where a mixture of two species having a fixed ADH:ALDH ratio may be formed in order to produce a third ratio at a desired different ratio from the two species. Although it is a mixture of two species, it is understood that three or more species may also be combined to produce a desired ratio between 1:3 and 1:51. The examples in the Table below show mixing of particular species; the calculations used may be extended to different combinations of species, which may be a mixture of two species or more than two species. Each composition has activity for degrading alcohol into a first and a second metabolite such that the present invention has the ability to degrade alcohol over an entire range from 1:3 to 1:51 of ADH:ALDH. The activity for alcohol/ethanol degradation is an intermediate activity between the activity of the two adjacent species. For example, the activity for an ADH:ALDH ratio of 1:4 is intermediate the activity for alcohol degradation of chicken (ADH:ALDH ratio of 1:3) and horse (ADH:ALDH ratio of 1:5)

The example below relates to the calculation of a formula of 1:6 ADH:ALDH using a combination of chicken having a ratio of 1:3 ADH:ALDH and donkey, having a ratio of 1:19 ADH to ALDH.

In 100 g of each extract:
chicken 25 g of ADH: 75 g of ALDH
donkey 5 g of ADH: 95 g of ALDH
To create a composition of 1:6 ADH:ALDH
Let x=amount of chicken extract
Let y=amount of donkey extract $$\frac{(\text{amount of } ALDH \text{ in new ratio})}{[(\text{amount of chicken } ADH)x + (\text{amount of donkey } ADH)y]} =$$

$$\frac{(\text{amount of } ADH \text{ in new ratio})}{[(\text{amount of chicken } ALDH)x + (\text{amount of donkey } ALDH)y]}$$

$$6(25x + 5y) = 1(75x + 95y)$$

$$150x + 30y = 75x + 95y$$

$$75x = 65y$$

$$x = (65/75)y$$

Therefore, the amount of chicken extract to donkey extract should be 0.86:1 to yield a ratio of 1:6 of ADH:ADLH.

Generally, the formula is:

$$\frac{(\text{amount of } ALDH \text{ in new ratio})}{[(\text{amount of species } A \ ADH)x + (\text{amount of spec. } B \ ADH)y]} =$$

$$\frac{(\text{amount of } ADH \text{ in new ratio})}{[(\text{amount of spec. } A \ ALDH)x + (\text{amount of species } B \ ALDH)y]}$$

where species A has a ratio below the desired new ratio and species B has a ratio above the desired new ratio and x is the amount of species A and y is the amount of species B. It is understood that this general equation may be expanded to include additional species, that is, a combination of three or more species.

Table 2, below, shows the ratios of different species that are combined to give each ratio point from 1:3 to 1:51 of ADH:ALDH. As stated above, other species combinations can also be used to achieve each of these data points. For example, although an ADH/ALDH ratio of 1:4 is obtained in the table from a combination of chicken and horse extracts, it can also be formed from a mixture of chicken and donkey extracts, chicken and cow, chicken and sheep, or chicken and lamb:

TABLE 2

| SPECIES OR MIXTURE OF SPECIES | MIX RATIO (FOR MIXTURE OF SPECIES) | ADH/ALDH RATIO |
|---|---|---|
| chicken | 100% chicken | 1:3 |
| chicken:horse | 1:0.37 | 1:4 |
| horse | 100% horse | 1:5 |
| chicken:donkey | 0.86:1 | 1:6 |
| chicken:donkey | 0.6:1 | 1:7 |
| chicken:donkey | 0.44:1 | 1:8 |
| chicken:donkey | 0.33:1 | 1:9 |
| chicken:donkey | 0.26:1 | 1:10 |
| chicken:donkey | 0.2:1 | 1:11 |
| chicken:donkey | 0.16:1 | 1:12 |
| chicken:donkey | 0.12:1 | 1:13 |
| chicken:donkey | 0.07:1 | 1:14 |
| chicken:donkey | 0.06:1 | 1:15 |
| chicken:donkey | 0.046:1 | 1:16 |
| chicken:donkey | 0.03:1 | 1:17 |
| chicken:donkey | 0.013:1 | 1:18 |
| donkey | 100% donkey | 1:19 |
| donkey:lamb | 9.5:1 | 1:20 |
| donkey:lamb | 4.5:1 | 1:21 |
| donkey:lamb | 2.8:1 | 1:22 |
| donkey:lamb | 2:1 | 1:23 |
| donkey:lamb | 1.5:1 | 1:24 |
| donkey:lamb | 1.17:1 | 1:25 |
| donkey:lamb | 0.93:1 | 1:26 |
| donkey:lamb | 0.75:1 | 1:27 |
| cow | 100% cow | 1:28 |
| donkey:lamb | 1:2 | 1:29 |
| donkey:lamb | 1:2.4 | 1:30 |
| donkey:lamb | 1:3 | 1:31 |
| donkey:lamb | 1:3.7 | 1:32 |
| donkey:lamb | 1:4.7 | 1:33 |
| donkey:lamb | 1:6 | 1:34 |
| donkey:lamb | 1:8 | 1:35 |
| donkey:lamb | 1:11.3 | 1:36 |
| donkey:lamb | 1:18 | 1:37 |
| donkey:lamb | 1:38 | 1:38 |
| lamb | 100% lamb | 1:39 |
| donkey:sheep | 1:5.0 | 1:40 |
| donkey:sheep | 1:5.7 | 1:41 |
| donkey:sheep | 1:6.6 | 1:42 |
| donkey:sheep | 1:7.8 | 1:43 |
| donkey:sheep | 1:9.3 | 1:44 |
| donkey:sheep | 1:11.3 | 1:45 |
| donkey:sheep | 1:14.0 | 1:46 |
| donkey:sheep | 1:18.2 | 1:47 |
| donkey:sheep | 1:25.1 | 1:48 |
| donkey:sheep | 1:39 | 1:49 |
| donkey:sheep | 1:80.6 | 1:50 |
| sheep | 100% sheep | 1:51 |

Although not shown in Table 2, it is also understood that the various ratios may be created using non-animal sources of ADH and ALDH, such as from Baker's yeast, as discussed above.

Example 11

In one aspect, the present invention produces a high-quality therapeutic enzyme remedy in an enteric capsule form to enhance degradation of alcohol in the human body, in order to relieve veisalgia and symptoms associated therewith for both casual and frequent alcohol drinkers. It is a freeze-dried powder from extract of bovine, ovine, equine or galline liver, or a mixture of extracts from different animals, by proprietary extraction and isolation methods that produce a product safe for human consumption and effective for alcohol degradation.

Using extraction and isolation methods, ADH and ALDH enzymes are successfully extracted from livers of different origin, including cow, lamb, sheep, horse, donkey, or chicken. The extracts were freeze-dried and stored as dried powder.

From the in-house stability test of the freeze-dried powder from bovine and ovine liver extract, it shows very good stability when stored more than 12 months at room temperature and dry humidity.

Figure 10:
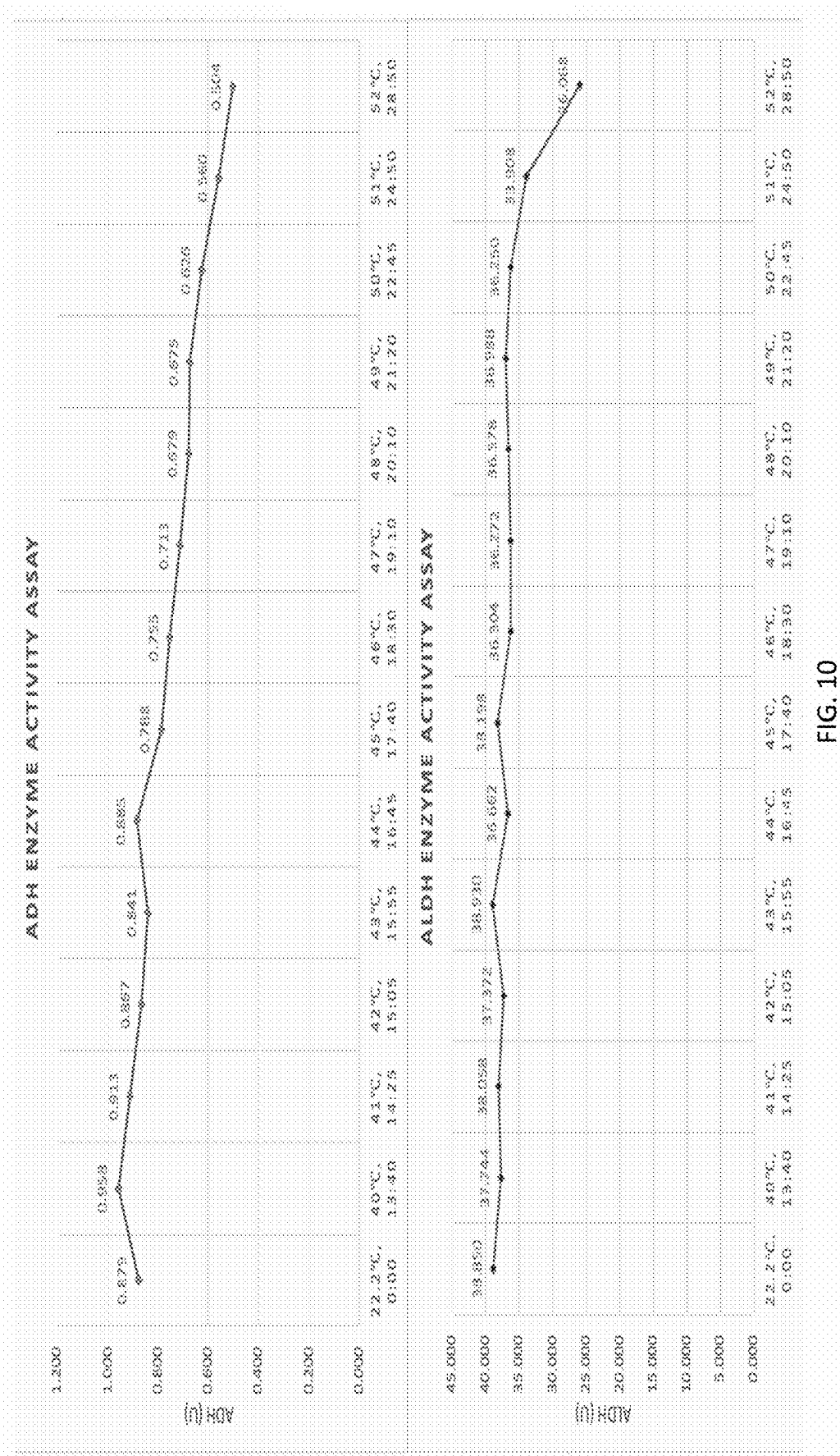
FIG. 10 shows the result of in vitro enzymatic activity of the contents of ADH and ALDH from cows' liver extract during heating of the extract.
Figure 11:
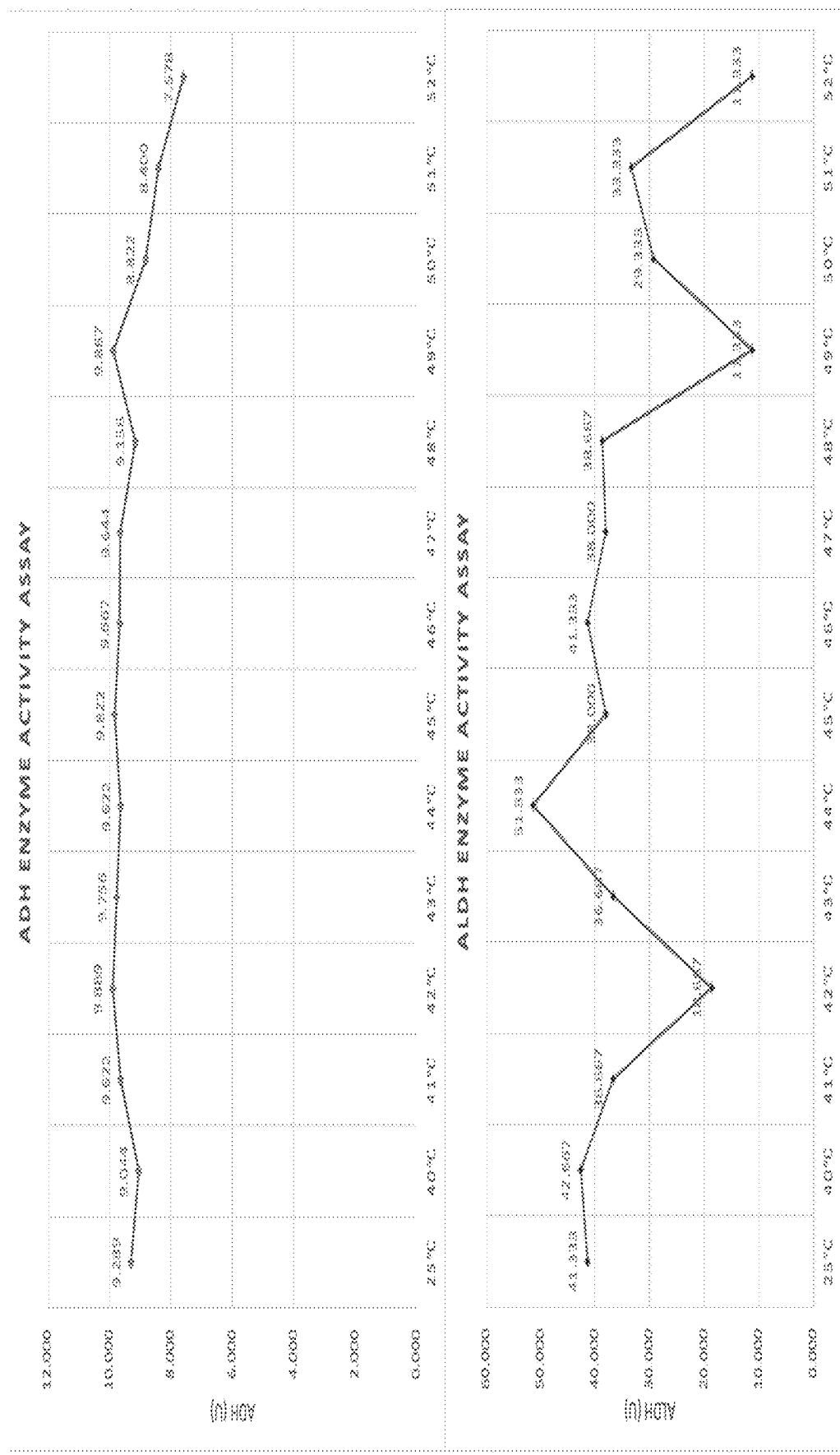
FIG. 11 shows the result of in vitro enzymatic activity of the contents of ADH and ALDH from horse liver extract during heating of the extract.
Figure 12:
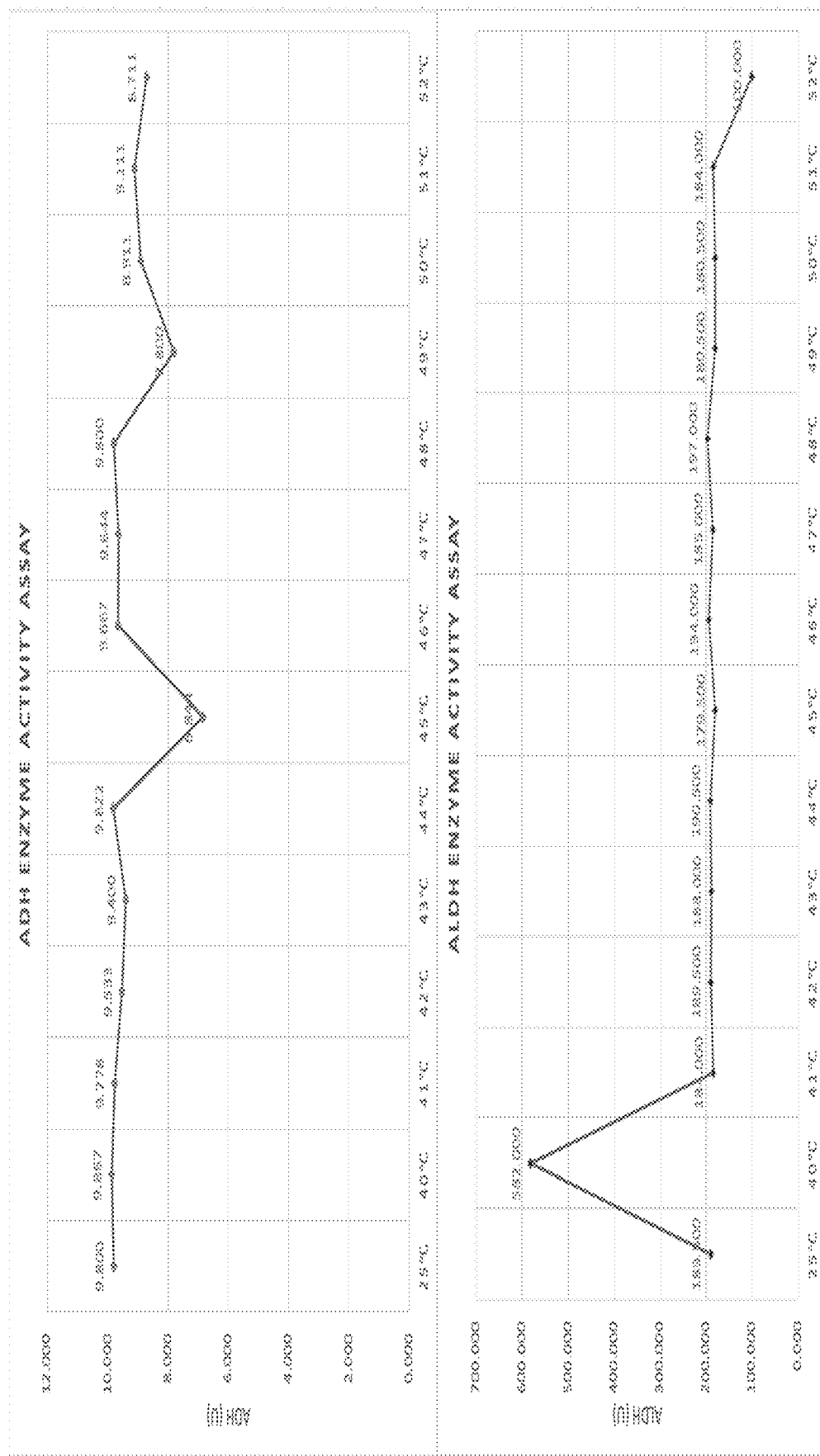
FIG. 12 shows the result of in vitro enzymatic activity of the contents of ADH and ALDH from donkey liver extract during heating of the extract.
Figure 13:
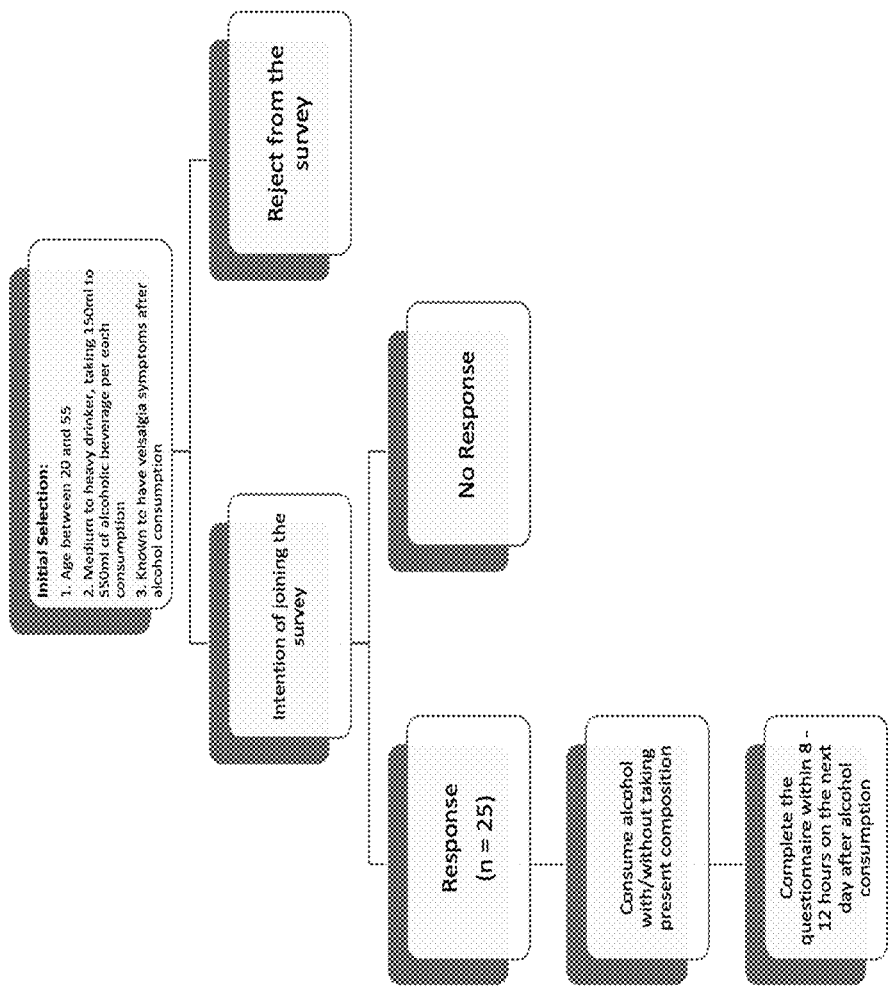
FIG. 13 shows the basic criteria of a survey to the effect of the present composition of this invention on the severity of veisalgia by using Alcohol Hangover Severity Scale (AHSS).
Figure 14:
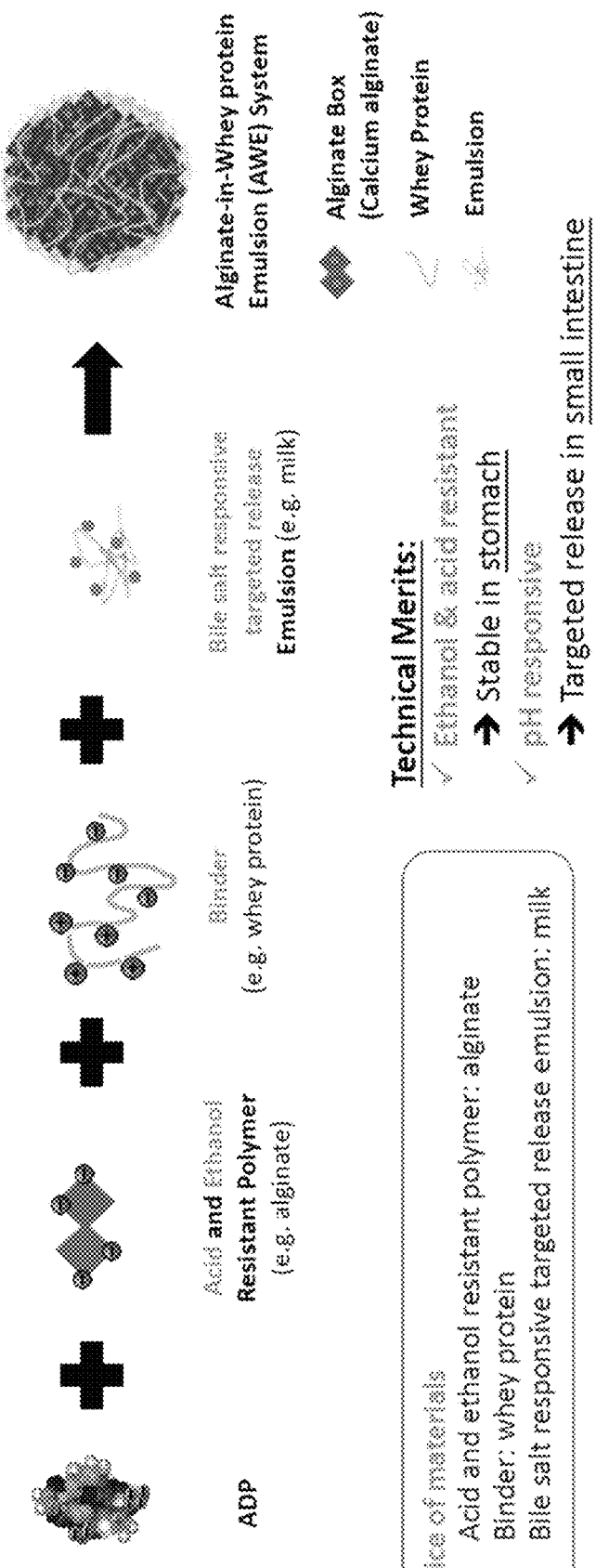
FIG. 14 is an overview of an alginate in whey protein emulsion system for microencapsulation depicting a final structure of the encapsulated material.
Figure 15:
FIG. 15 shows ADH:ALDH ratios in different batches of crude extracts.
Figure 16:
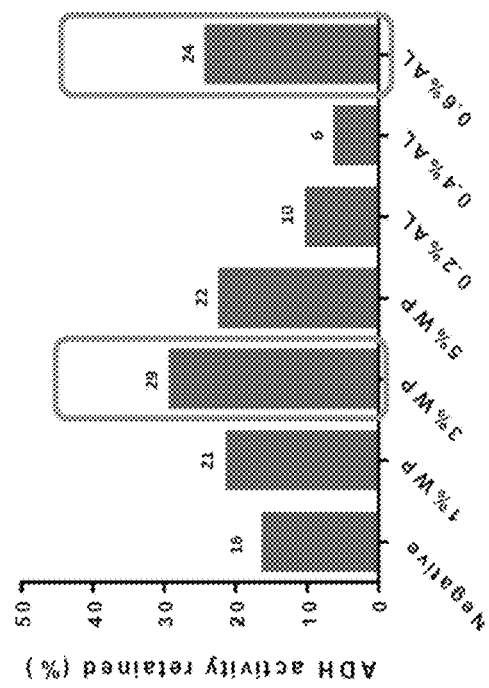
FIG. 16 shows the encapsulation effect of different concentrations of polymer and binder on ADH activity for the compositions of the present invention.
Figure 16:
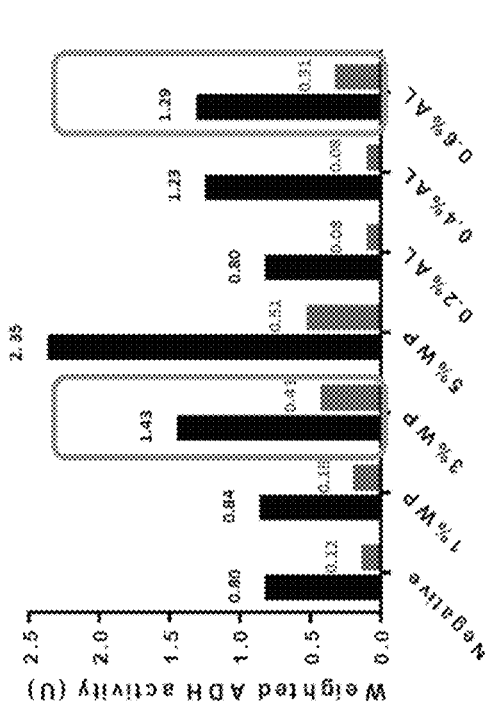
Figure 17:
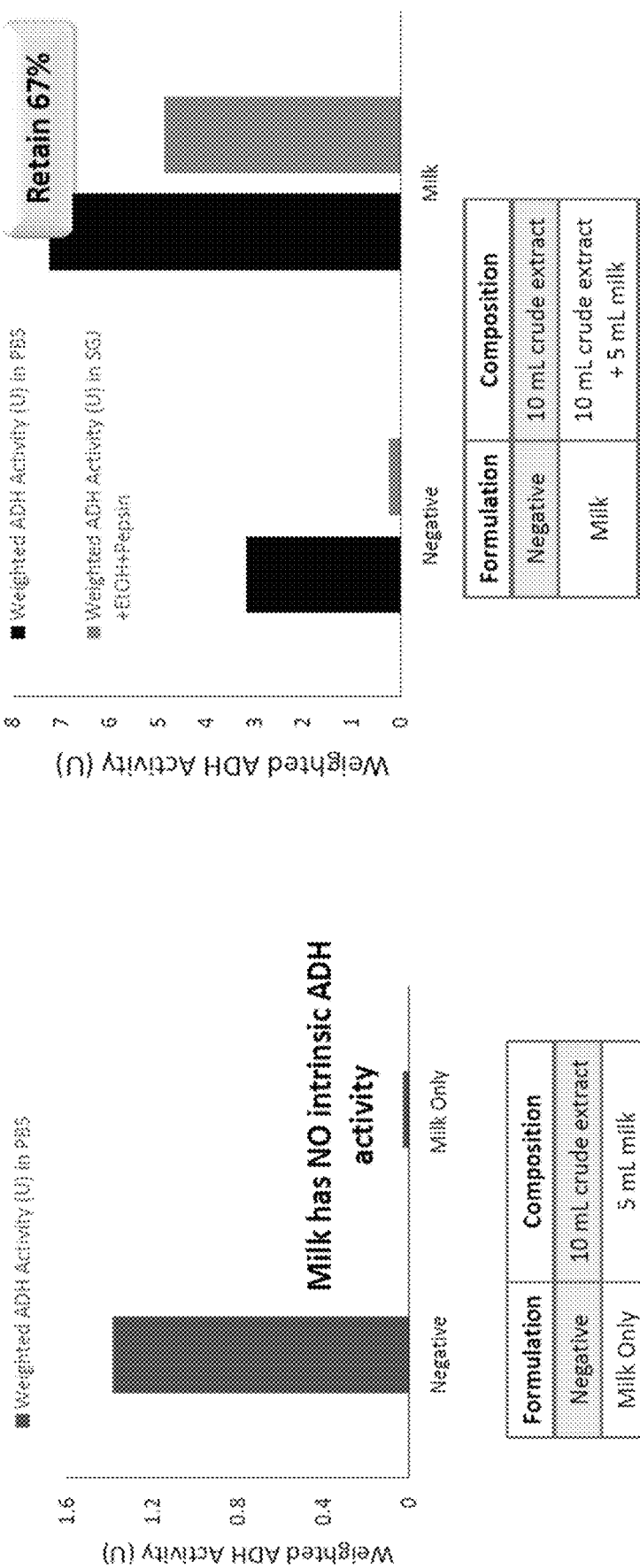
FIG. 17 shows the encapsulation effect of emulsion on ADH activity in an acid-ethanol resistance assay.
Figure 18:
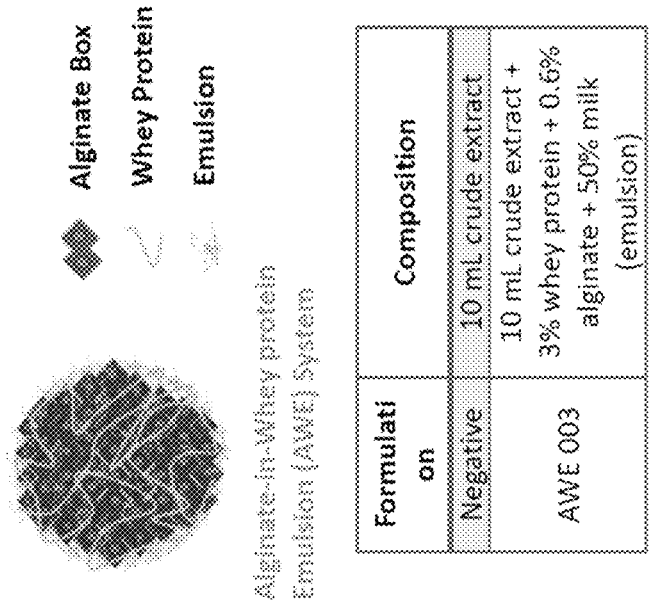
FIG. 18 depicts formulation components for encapsulation.
Figure 19:
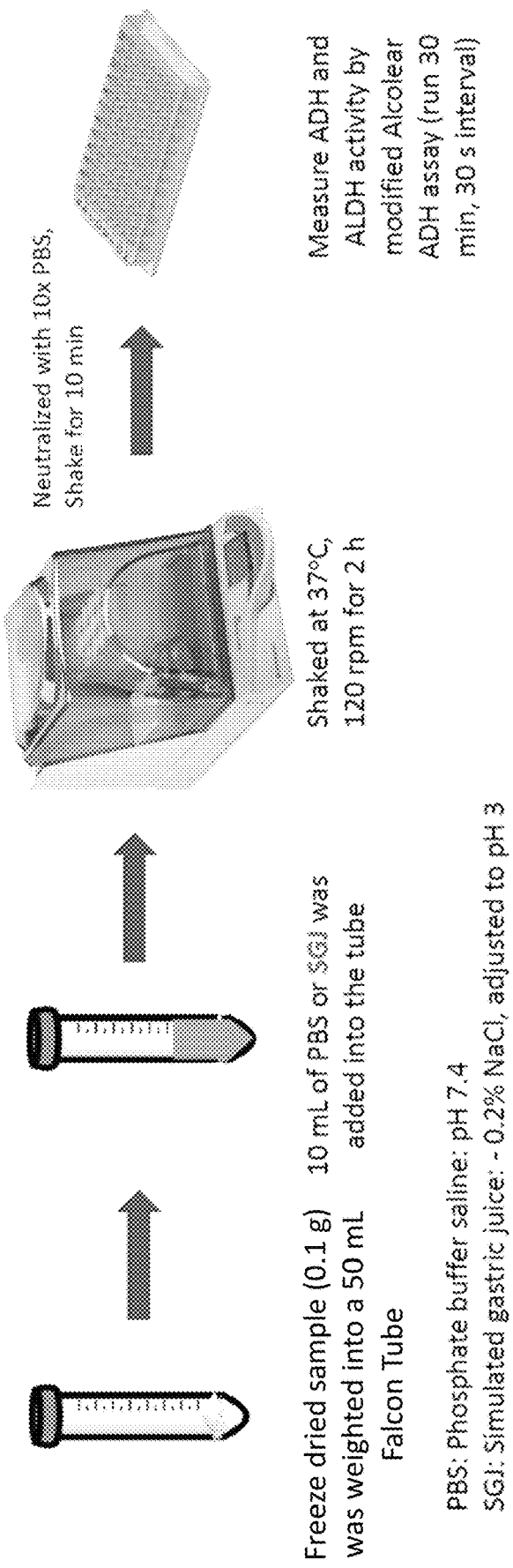
FIG. 19 illustrates configurations for testing the encapsulation effect of the AWE system on ADH and ALDH activity of the inventive compositions in an acid resistance assay.
Figure 20:
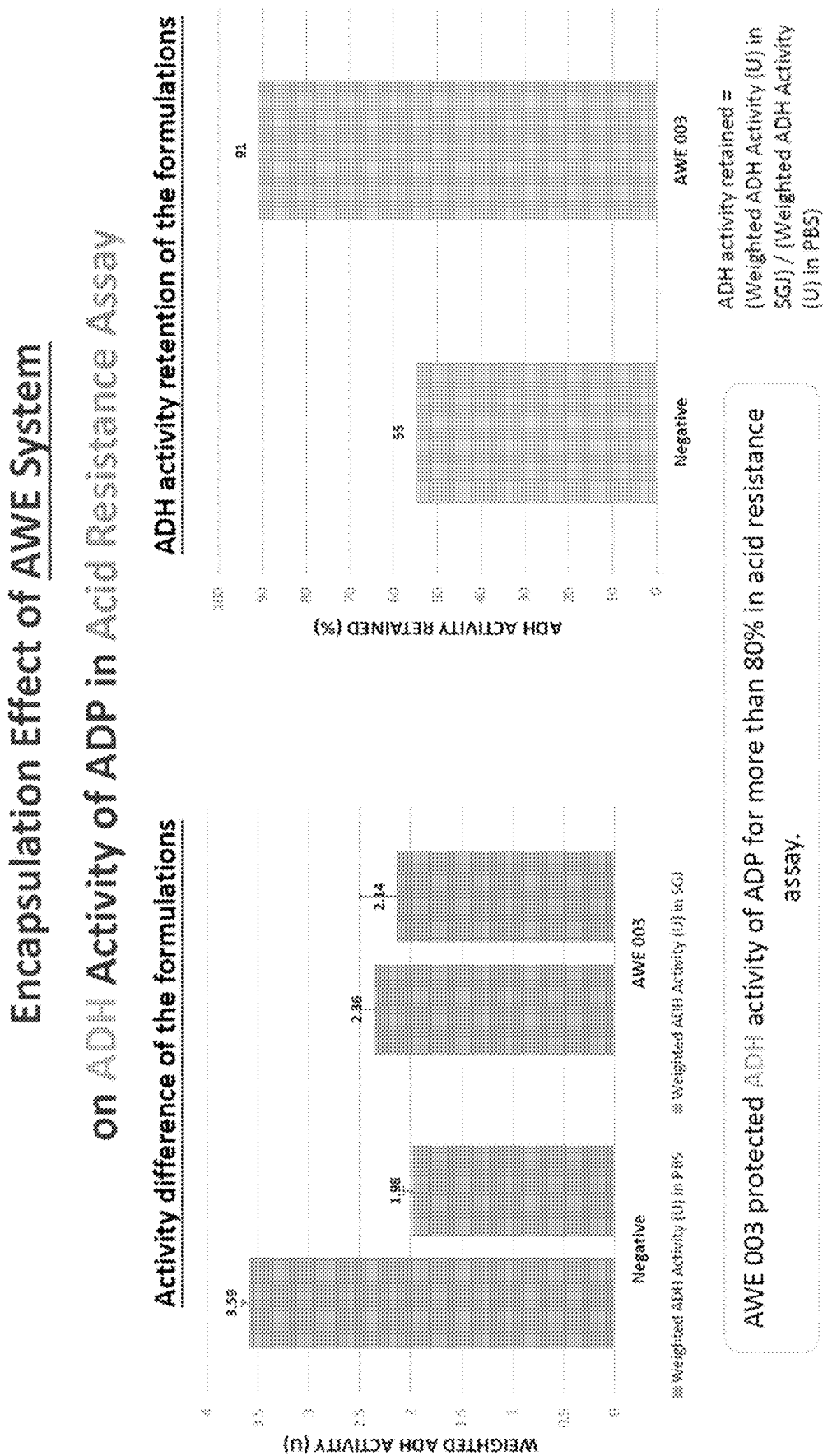
FIG. 20 shows the encapsulation effect of an AWE 003 composition on ADH activity of the composition in an acid resistance assay.
Figure 21:
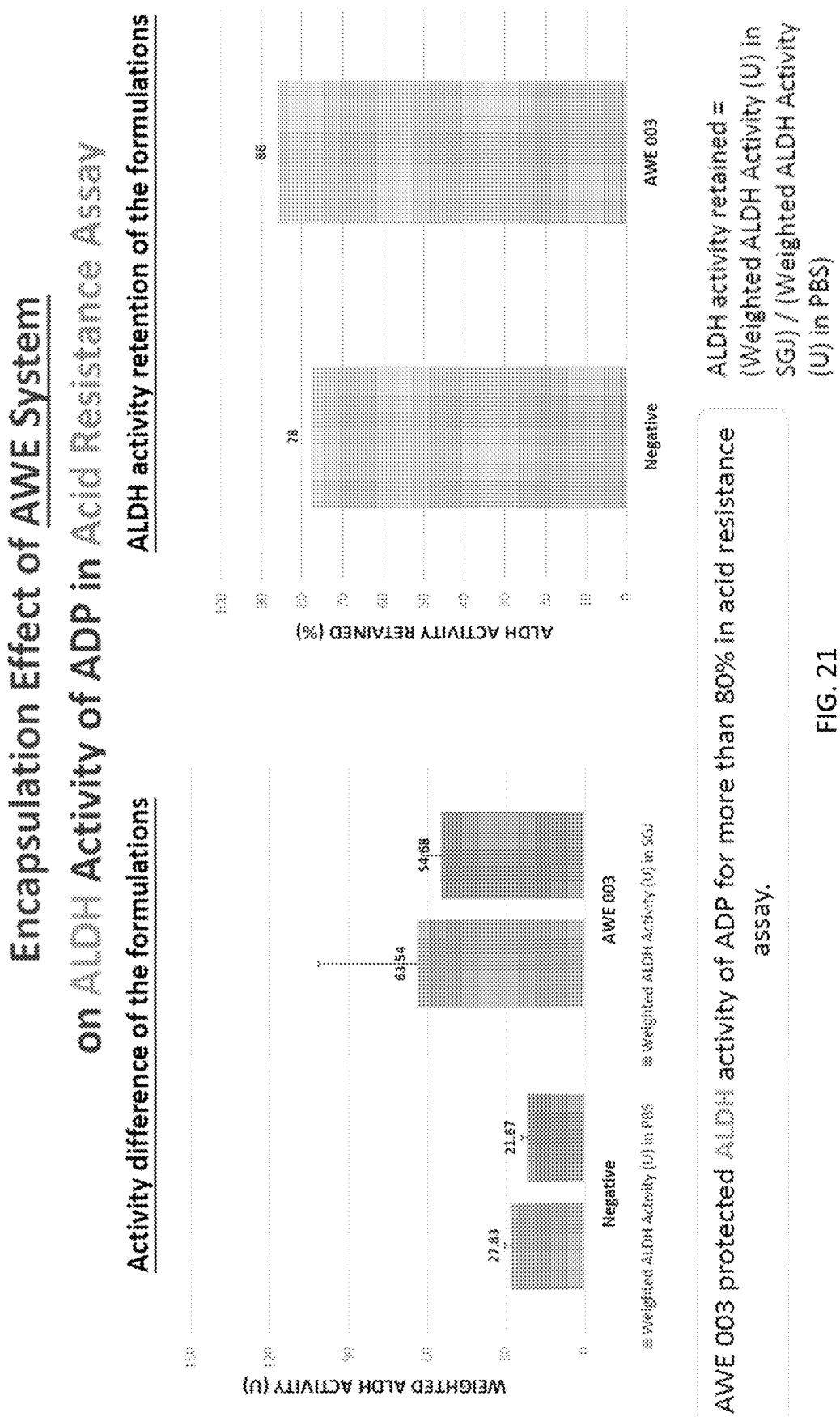
FIG. 21 shows the encapsulation effect of the AWE 003 composition on ALDH activity of the inventive composition in an acid resistance assay.
Figure 22:
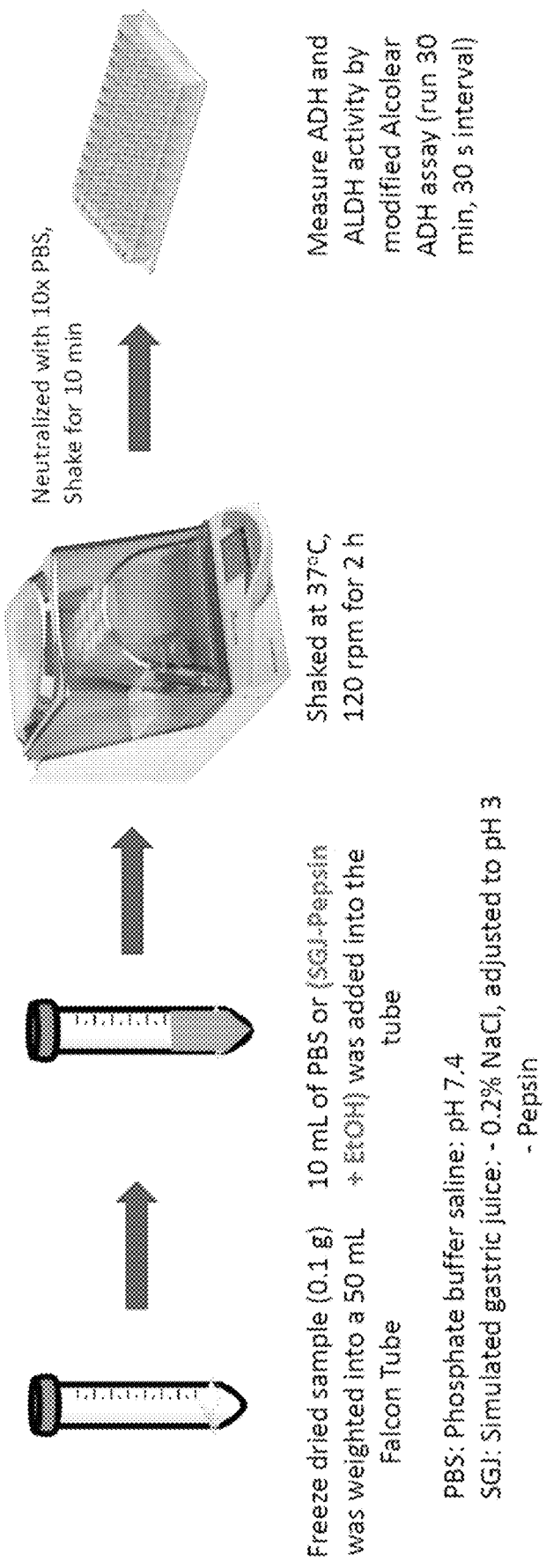
FIG. 22 shows the experimental set up for testing the encapsulation effect of the AWE system on ADH and ALDH activity of the composition in an acid-ethanol resistance assay.
Figure 23:
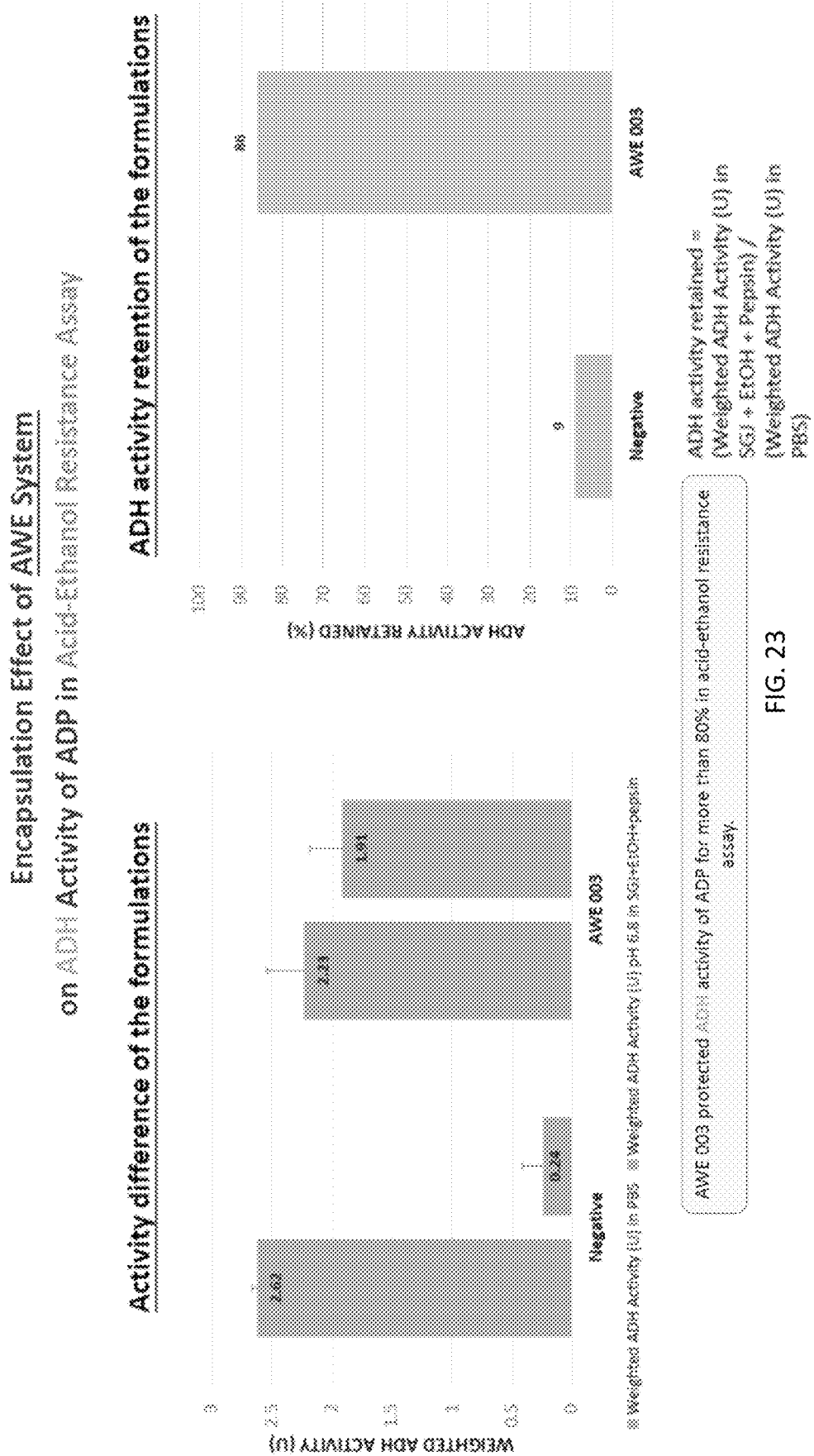
FIG. 23 shows a further description of the AWE 003 composition encapsulation effect on ADH activity in an acid-ethanol resistance assay.
Figure 24:
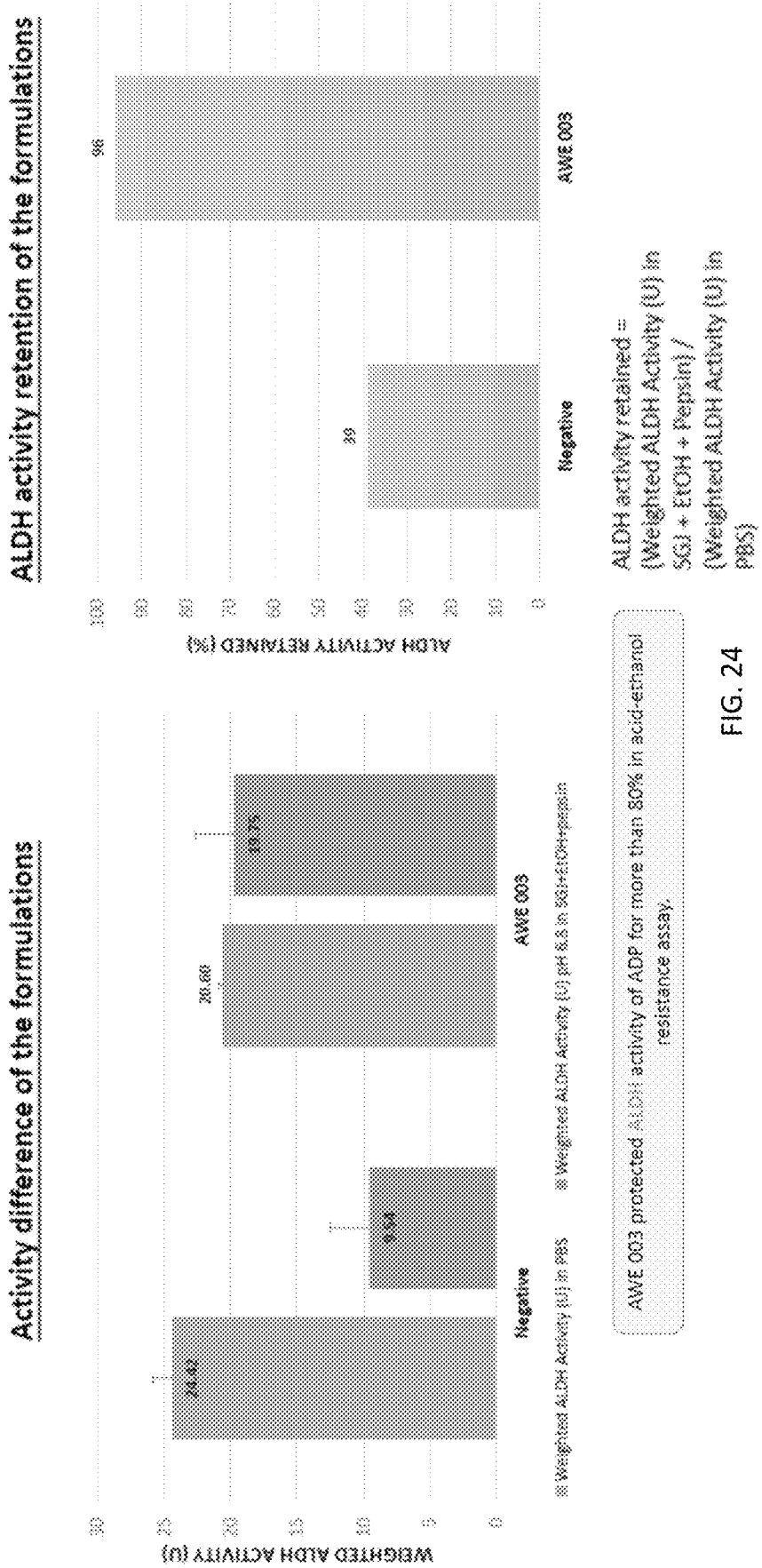
FIG. 24 shows the encapsulation effect of the AWE 003 composition on ALDH activity of the composition in an acid-ethanol resistance assay.
Figure 25:
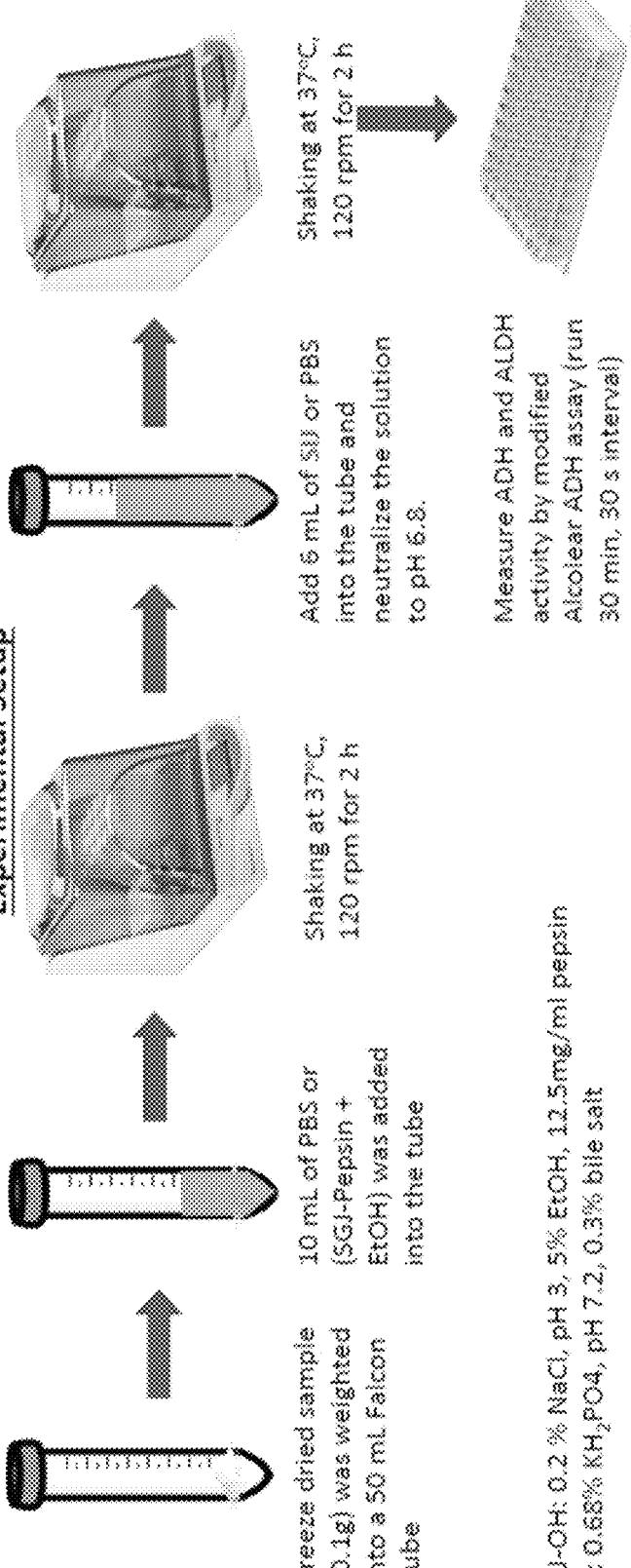
FIG. 25 shows the experimental setup for testing the encapsulation effect of AWE system on ADH and ALDH activity of the composition in a targeted release assay.
Figure 26:
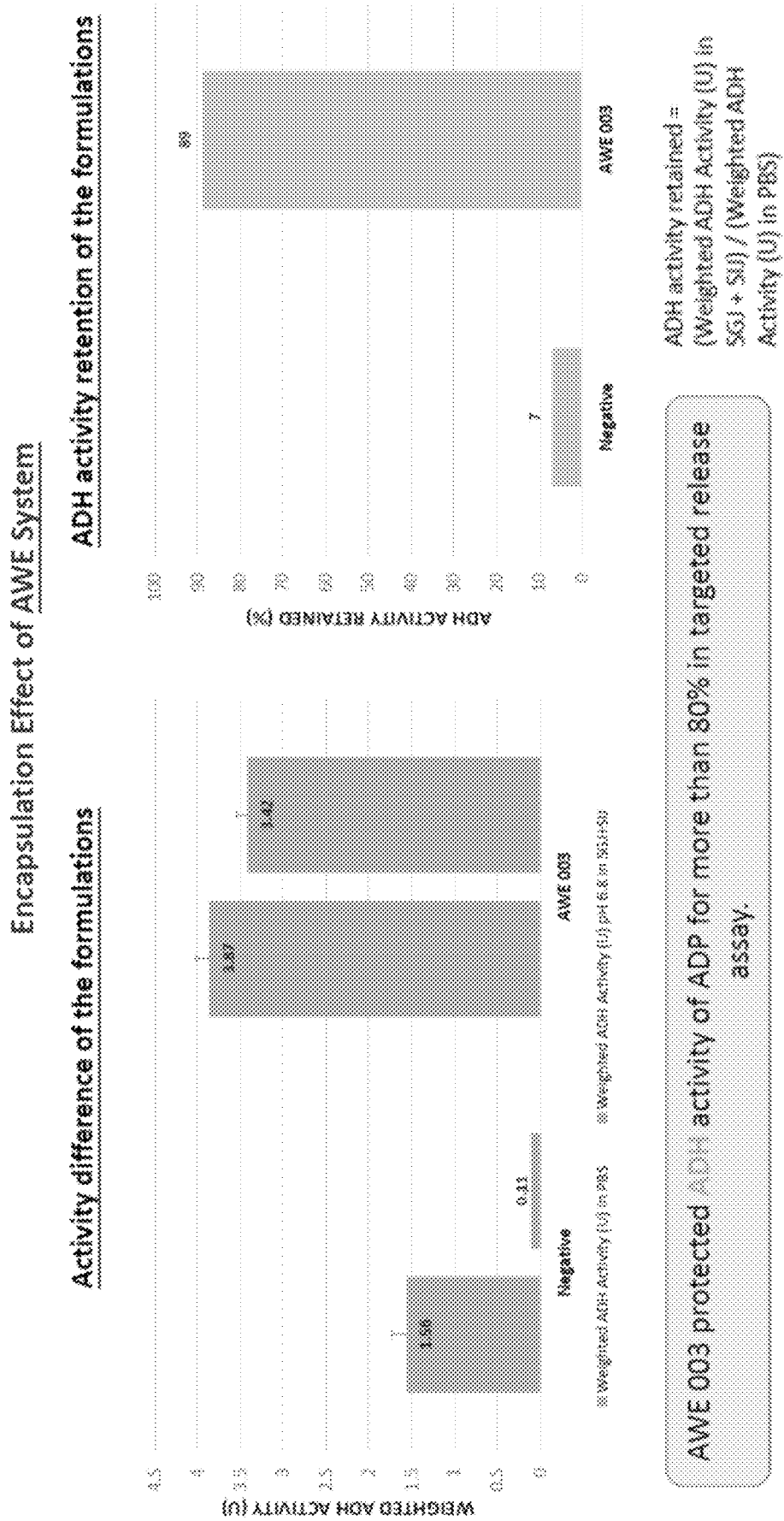
FIG. 26 shows the encapsulation effect of the 003 composition on ADH activity of the composition in a targeted release assay.
Figure 27:
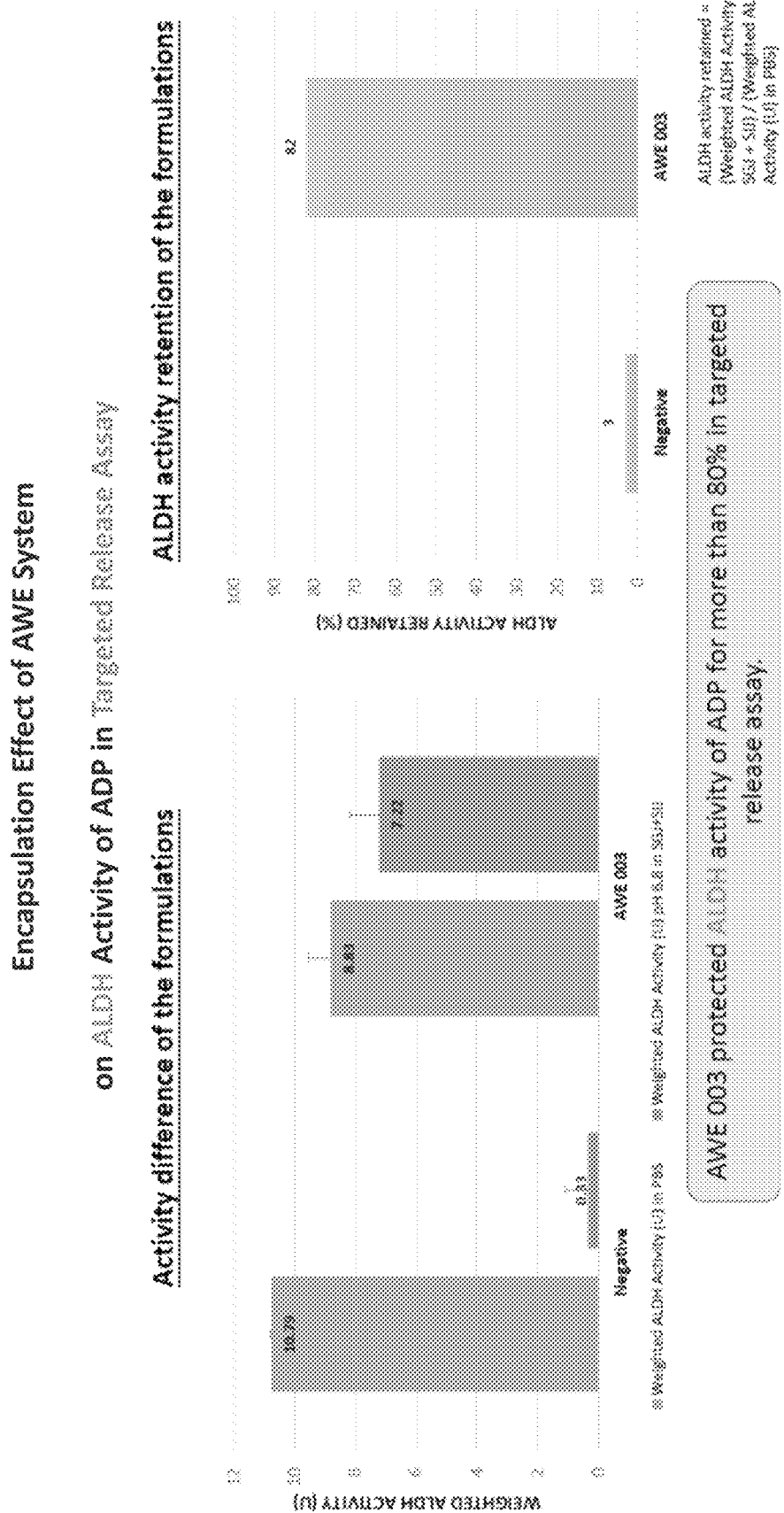
FIG. 27 shows an encapsulation effect of the AWE 003 on ALDH activity of the inventive composition in a targeted release assay.

The present invention uses an inventive extraction method. The inventive extraction includes precise control of the heating and cooling of the extract from mammalian or aves livers. It is found that when the extract from livers was heated to 40° C., an extract with the highest content of ADH, together with ADH and ALDH enzymes contents in the molar ratio range from approximately 1:3 to approximately 1:51, can be obtained. The in vitro enzymatic activity of contents of ADH and ALDH from the liver extract of cows, horse and donkey in this heating process are illustrated in FIG. 10 to FIG. 12.

Therefore, the therapeutic enzyme of the present invention could not be produced from the livers of pig, duck, or goose. From an in vitro study of the present invention, ALDH was not present in the liver extract from pig, duck, or goose, where ALDH is one of the main components in the present composition.

Optionally, the extracted enzymes may be packaged with antioxidants in enteric capsules. Antioxidants, along with other optional excipients, can protect the enzymes from degradation in order to maintain a longer shelf-life with maximum efficacy.

Examples II: Effect of the Compositions on Alcohol Metabolism

Oral supplements according to the present invention may be used in the following manner:
  i. To enhance alcohol metabolism in the human body in order to relieve veisalgia and symptoms associated therewith.
  ii. To degrade alcohol to prevent Alcoholic Liver Disease ("ALD") and non-alcoholic fatty liver disease (NAFLD).

Two surveys were conducted by selecting subjects fulfilling the basic criteria shown in FIG. 11 to evaluate the effect of the present composition of this invention on the severity of veisalgia by using Alcohol Hangover Severity Scale (AHSS).

Survey 1—Test of Freeze-Dried Powder from Cows' Liver Extract (ADH:ALDH 1:28) Encapsulated in Enteric Capsule:

Twenty-five subjects were successfully recruited and were asked to complete the same questionnaire twice during the 1-month test period. The subjects drank 150 ml to 550 ml of an alcoholic beverage with an alcohol content ranging from 15% to 55% along with food. The questionnaire was completed on the next day 8-12 hours after the alcohol consumption, where one questionnaire for each subject was completed under their normal alcohol intake practice, and the other was completed with taking the freeze-dried powder from cow's liver extract encapsulated in enteric capsule before alcohol consumption. Twelve symptoms including fatigue, apathy, concentration problems, clumsiness, confusion, thirst, sweating, shivering, stomach pain, nausea, dizziness, and heart pounding were used to evaluate the severity of veisalgia for all subjects The subjects were asked to indicate to what extent they experienced the 12 symptoms mentioned above after they woke up. It can be seen that 2 subjects did not develop veisalgia and/or any symptoms associated therewith, no matter with or without taking the above mentioned composition during the test period; 22 subjects developed veisalgia and/or symptoms associated therewith, in the absence of the above mentioned composition, but veisalgia or the associated symptoms was/were relieved after taking the above mentioned composition; 1 subject developed veisalgia and the associated symptoms, whether or not the above mentioned composition was taken. From the AHSS survey, about 88% of the subjects had a positive response towards to the above-mentioned composition, with significant relief of their veisalgia and the associated symptoms after the alcohol consumption.

Survey 2—Test of Freeze-Dried Powder from Donkey Liver Extract (ADH:ALDH 1:19) Encapsulated in Enteric Capsule:

Nine subjects were successfully recruited and were asked to complete the same questionnaire twice during the 1-month test period. The subjects drank 100 ml to 300 ml of alcoholic beverage with alcohol content ranging from 50% to 53% with food. The questionnaire was completed on the next day 8-12 hours after alcohol consumption, where one questionnaire for each subject was completed under their normal alcohol intake practice, and the other was completed after taking the freeze-dried powder from donkey liver extract encapsulated in enteric capsule before alcohol consumption. Twelve symptoms including fatigue, apathy, concentration problems, clumsiness, confusion, thirst, sweating, shivering, stomach pain, nausea, dizziness, and heart pounding were used to evaluate the severity of veisalgia for all subjects The subjects were asked to indicate to what extent they experienced the 12 symptoms mentioned above after they woke up. It can be seen that 8 subjects developed veisalgia and/or symptoms associated therewith, in the absence of the above-mentioned composition, but veisalgia or the associated symptoms was/were relieved after taking the above-mentioned composition; 1 subject developed mild veisalgia and the associated symptoms, whether or not the above-mentioned composition was taken. From the AHSS survey, about 89% of the subjects had a positive response towards to the above-mentioned composition, with significant relief of their veisalgia and the associated symptoms after the alcohol consumption.

As determined from the plots in FIG. 2 to FIG. 7, the equilibrium mid-point of ethanol and acetate from the in vitro tests were determined. The equilibrium mid-points are listed in Table 3.

TABLE 3

| Animal | Ratio ADH:ALDH | Equilibrium mid point (seconds) |
| --- | --- | --- |
| Cows | 1:28 | 88 |
| Lamb | 1:39 | 100 |
| Sheep | 1:51 | 102 |
| Horse | 1:5 | 75 |
| Donkey | 1:19 | 73 |
| Chicken | 1:3 | 95 |

From the data in Table 3, it can be seen that even though the ratios of ADH:ALDH vary from 1:3 to 1:51 from the 6 animals (cows, lamb, sheep, horse, donkey, and chicken), each ADH:ALDH ratio demonstrates a similar equilibrium mid-point for ethanol and acetate. That is, the in vitro experiments indicate that all ratios are effective on breaking down alcohol, and then acetaldehyde, into their respective metabolites, at approximately the same rate without the accumulation of the first metabolites. Further, the results of the two surveys set forth above show substantially similar reductions in veisalgia symptoms for ADH:ALDH of 1:19 and 1:28. Therefore, based on the similar equilibrium mid-points and the human survey results, it has been determined that the breakdown of metabolites is efficacious over the entire range from 1:3 to at least 1:51. Consequently, the different ratios of ADH:ALDH in the range from 1:3 to 1:51 in the composition will be efficacious in reducing veisalgia symptoms. Further, based on these same metabolic mechanisms, the compositions may be effective in reducing or preventing NAFLD.

At higher doses, the enzyme compositions of the present invention may be used as an oral or injectable medication which can rapidly remove alcohol in emergency situations of acute alcohol intoxication. The present composition can reduce and prevent the severity of acute alcohol intoxication by efficiently converting alcohol to non-harmful substances before body tissues and organs, for instance, liver, uptake harmful levels of alcohol from blood.

For injectable formulations and optionally for oral formulations, recombinant DNA technology by introducing mammalian expression vectors carrying genes of human h-ADH and h-ALDH into safe and well-studied mammalian cell lines may be employed. These mammalian-cells-expressed target enzymes are further isolated and purified by chromatographic techniques. The present invention is useful to produce clinical grade h-ADH and h-ALDH for effective intravenous ("I.V.") or intramuscular ("I.M.") infusion of therapeutic enzyme remedies for emergency use in hospitals and clinics.

The human genome includes 19 ALDH genes. ALDH1 is primarily found in the liver and may be used in the enzyme extract version of the present invention. Another ALDH is ALDH2 which is found in the mitochondria. ALDH2 may be selected as the ALDH used in the present invention; its sequence is represented by SEQ ID NO: 1:

```
MSAAATQAVP APNQQPEVFC NQIFINNEWH DAVSRKTFPT

VNPSTGEVIC

QVAEGDKEDV DKAVKAARAA FQLGSPWRRM DASHRGRLLN

RLADLIERDR

TYLAALETLD NGKPYVISYL VDLDMVLKCL RYYAGWADKY

HGKTIPIDGD FFSYTRHEPV

GVCGQIIPWN FPLLMQAWKL GPALATGNVV VMKVAEQTPL

TALYVANLIK EAGFPPGVVN

IVPGFGPTAG AAIASHEDVD KVAFTGSTEI GRVIQVAAGS

SNLKRVTLEL GGKSPNIIMS

DADMDWAVEQ AHFALFFNQG QCCCAGSRTF VQEDIYDEFV

ERSVARAKSR

VVGNPFDSKT EQGPQVDETQ FKKILGYINT GKQEGAKLLC

GGGIAADRGY FIQPTVFGDV

QDGMTIAKEE IFGPVMQILK FKTIEEVVGR ANNSTYGLAA

AVFTKDLDKA NYLSQALQAG

TVWVNCYDVF GAQSPFGGYK MSGSGRELGE YGLQAYTEVK

TVTVKVPQKN S
```

Recombinant ALDH such as ALDH2 is commercially available from suppliers such as Sigma Aldrich. Examples of recombinant techniques to produce ALD and ALDH are described in Nene et al., J. Biomed. Sci. 2017, 24:3, published 5 Jan. 2017, the disclosure of which is incorporated by reference herein.

The active ingredients in the formulation of the present invention may be incorporated into an oral formulation that may be administered as a dietary supplement product. A potential health benefit of this product is to relieve veisalgia and the associated symptoms for casual and frequent alcohol drinkers. The product should be taken before consuming alcohol.

Examples III: Encapsulation

As set forth above, the gastric acid and ethanol resistant property of the encapsulation system is provided from polysaccharides, such as alginate while the amphoteric binder provided from protein, such as whey protein. A targeted release property is provided from a casein-include emulsion, such as using milk for the casein proteins.

The percentage of these components in the encapsulation formulations is typically 0.6% w/v or less of alginate, 5% w/v of whey protein, 50% w/v or less milk.

A particular formulation is 0.6% w/v alginate, 3% w/v whey protein and 50% w/v milk. In the Examples of FIGS. 14-27, this composition is designated as AWE 003.

The method of producing the AWE formulation for protecting the ADH:ALDH-containing material includes:

Preparing a homogenous protective AWE formulation with alginate, whey protein and milk using stir-mixing method;

Encapsulating the ADH:ALDH-containing material with the AWE protective formulation sequentially using stir-mixing method.

The particle size of the encapsulated ADH:ALDH-containing material is in the range of 0.2-2 mm, more preferable less than 1 mm.

The safety of claim 1 formulation is compliant with acute toxicity, heavy metals testing and microbiological quality assessments standard.

The enzyme activities of the encapsulated ADH:ALDH-containing material (ADH and ALDH enzyme activities), has a conversion of NAD+ to NADH no less than 80% under the following conditions:

Acid resistance assessment: 2-hr incubation in simulated gastric juice (pH 3.0, 37° C.).

Ethanol and acid resistance assessment: 2-hr incubation in simulated gastric juice (pH 3.0, 37° C.) containing ethanol;

Targeted release assessment: 2-hr incubation in simulated gastric juice (pH 3.0, 37° C.) containing ethanol followed by 2-hr incubation in simulated small intestinal condition (simulated small intestinal juice, pH 6.8, 37° C.).

The ADH:ALDH-containing material activities (ADH and ALDH enzyme activities) in terms of the conversion of NAD+ to NADH have not more than 20% reduction after subjected to an accelerated stability test at 40±2° C., RH 75±5% for 3 months. Additional testing is performed for stability in real-time study at 25±2° C. at RH 65±5° C. for 6 months.

FIGS. 14-27 depict the techniques used for encapsulation of the ADP compositions (ADH:ALDH-containing material) described above. It further shows measurements of the ADH:ALDH for various encapsulant compositions demonstrating that the system does not degrade the activity of the material while being resistant to both stomach acid and ethanol. In particular, these FIGS. demonstrate that composition AWE 003 showed good properties in terms of stability and lack of degradation of the ADP compositions.

An oral composition that includes the encapsulated ADH:ALDH composition may be used in this encapsulated format. Optionally, one or more particles of the encapsulated composition may be further encapsulated in a conventional capsule material, such as gelatin or other known capsule materials, for ease of swallowing and for providing a uniform oral product size and dosage.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

As used herein and not otherwise defined, the terms "substantially," "substantial," "approximately" and "about" are used to describe and account for small variations. When used in conjunction with an event or circumstance, the terms can encompass instances in which the event or circumstance occurs precisely as well as instances in which the event or circumstance occurs to a close approximation. For example, when used in conjunction with a numerical value, the terms can encompass a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. The term "substantially coplanar" can refer to two surfaces within micrometers of lying along a same plane, such as within 40 µm, within 30 µm, within 20 µm, within 10 µm, or within 1 µm of lying along the same plane.

As used herein, the singular terms "a," "an," and "the" may include plural referents unless the context clearly dictates otherwise. In the description of some embodiments, a component provided "on" or "over" another component can encompass cases where the former component is directly on (e.g., in physical contact with) the latter component, as well as cases where one or more intervening components are located between the former component and the latter component.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not necessarily be drawn to scale. There may be distinctions between the artistic renditions in the present disclosure and the actual apparatus due to manufacturing processes and tolerances. There may be other embodiments of the present disclosure which are not specifically illustrated. The specification and the drawings are to be regarded as illustrative rather than restrictive. Modifications may be made to adapt a particular situation, material, composition of matter, method, or process to the objective, spirit, and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations.

The invention claimed is:

1. An encapsulated composition for converting ethanol to acetaldehyde and subsequently converting the acetaldehyde to acetate, the composition comprising alcohol dehydrogenase and aldehyde dehydrogenase in a molar ratio of approximately 1:3 to approximately 1:51, the composition being encapsulated by a polysaccharide-whey-casein encapsulant such that the encapsulated composition is an orally-administered controlled release composition in the small intestine.

2. The encapsulated composition of claim 1, wherein the alcohol dehydrogenase and aldehyde dehydrogenase are sourced from the same or two or more different animal origins.

3. The encapsulated composition of claim 2, wherein the alcohol dehydrogenase and aldehyde dehydrogenase are sourced from the same animal origin, and the animal is selected from bovine, ovine, equine, or galline.

4. The encapsulated composition of claim 3, wherein the alcohol dehydrogenase and aldehyde dehydrogenase are sourced from different animal origins, and the animals is selected from two or more of bovine, ovine, equine, galline or any combination thereof.

5. The encapsulated composition of claim 3, wherein the alcohol dehydrogenase and aldehyde dehydrogenase are sourced from the livers of the animals.

6. The encapsulated composition of claim 1, wherein the alcohol dehydrogenase and aldehyde dehydrogenase are sourced from Baker's yeast (*S. cerevisiae*).

7. The encapsulated composition of claim 1, wherein the encapsulated composition includes 0.6% w/v alginate or less, 5% w/v whey protein or less and 50% w/v milk or less, with a balance being alcohol dehydrogenase and aldehyde dehydrogenase in a molar ratio of approximately 1:3 to approximately 1:51.

8. The encapsulated composition of claim 1, wherein a particle size of the encapsulated composition is in a range of 0.2-2 mm.

9. The encapsulated composition of claim 1, wherein the polysaccharide is one or more of alginate, chitosan, pectin, starch, cellulose, agarose, xanthan gum, carrageenan, or guar gum.

10. The encapsulated composition of claim 1, wherein the polysaccharide is sodium alginate.

11. A method of preparing the encapsulated composition of claim 1, comprising:
   forming a mixture of polysaccharide, whey, and milk;
   introducing the alcohol dehydrogenase and aldehyde dehydrogenase composition in a molar ratio of approximately 1:3 to approximately 1:51 to the mixture;
   forming particles of the alcohol dehydrogenase and aldehyde dehydrogenase composition in a molar ratio of approximately 1:3 to approximately 1:51 surrounded by the encapsulant formed from the polysaccharide, whey, and milk mixture.

12. The method of claim 11, wherein the polysaccharide is sodium alginate.

* * * * *

SEQUENCE LISTING

```
Sequence total quantity: 1
SEQ ID NO: 1             moltype = AA  length = 501
FEATURE                  Location/Qualifiers
source                   1..501
                         mol_type = protein
                         organism = Homo sapiens
SEQUENCE: 1
MSAAATQAVP APNQQPEVFC NQIFINNEWH DAVSRKTFPT VNPSTGEVIC QVAEGDKEDV  60
DKAVKAARAA FQLGSPWRRM DASHRGRLLN RLADLIERDR TYLAALETLD NGKPYVISYL 120
VDLDMVLKCL RYYAGWADKY HGKTIPIDGD FFSYTRHEPV GVCGQIIPWN FPLLMQAWKL 180
GPALATGNVV VMKVAEQTPL TALYVANLIK EAGFPPGVVN IVPGFGPTAG AAIASHEDVD 240
KVAFTGSTEI GRVIQVAAGS SNLKRVTLEL GGKSPNIIMS DADMDWAVEQ AHFALFFNQG 300
QCCCAGSRTF VQEDIYDEFV ERSVARAKSR VVGNPFDSKT EQGPQVDETQ FKKILGYINT 360
GKQEGAKLLC GGGIAADRGY FIQPTVFGDV QDGMTIAKEE IFGPVMQILK FKTIEEVVGR 420
ANNSTYGLAA AVFTKDLDKA NYLSQALQAG TVWVNCYDVF GAQSPFGGYK MSGSGRELGE 480
YGLQAYTEVK TVTVKVPQKN S                                          501
```